(12) United States Patent
Frigg et al.

(10) Patent No.: US 8,157,806 B2
(45) Date of Patent: Apr. 17, 2012

(54) APPARATUS AND METHODS FOR VERTEBRAL AUGMENTATION

(75) Inventors: Robert Frigg, Bettlach (CH); Christof Dutoit, Solothurn (CH); Andreas Appenzeller, Biel (CH); Thierry Stoll, Meinisberg (CH); Alfred Benoit, Lengnau (CH); Christoph Fuerst, Zuchwil (CH); Paul Heini, Wabern (CH)

(73) Assignee: Synthes USA, LLC, West Chester, PA (US)

( * ) Notice: Subject to any disclaimer, the term of this patent is extended or adjusted under 35 U.S.C. 154(b) by 782 days.

(21) Appl. No.: 11/546,579

(22) Filed: Oct. 10, 2006

(65) Prior Publication Data

US 2007/0093846 A1  Apr. 26, 2007

Related U.S. Application Data

(60) Provisional application No. 60/725,773, filed on Oct. 12, 2005, provisional application No. 60/726,835, filed on Oct. 13, 2005, provisional application No. 60/728,442, filed on Oct. 19, 2005, provisional application No. 60/730,909, filed on Oct. 27, 2005, provisional application No. 60/733,026, filed on Nov. 3, 2005.

(51) Int. Cl.
*A61B 17/70* (2006.01)

(52) U.S. Cl. .......... 606/86 A; 606/279; 606/246

(58) Field of Classification Search .......... 606/57, 606/86 A, 86 R, 279, 90, 92, 105; 623/17.11–17.16
See application file for complete search history.

(56) References Cited

U.S. PATENT DOCUMENTS

| | | | |
|---|---|---|---|
| 4,611,581 A | 9/1986 | Steffee | |
| 5,397,322 A | 3/1995 | Campopiano | 606/57 |
| 5,425,732 A | 6/1995 | Ulrich | 606/61 |
| 5,782,831 A | 7/1998 | Sherman et al. | |
| 6,235,043 B1 | 5/2001 | Reiley et al. | |

(Continued)

FOREIGN PATENT DOCUMENTS

EP   1308134   7/2003

(Continued)

OTHER PUBLICATIONS

Fürderer et al., "Vertebral body stenting," Orthopäde 31:356-361 (2002) (in German, with English language translation).

(Continued)

*Primary Examiner* — Eduardo C Robert
*Assistant Examiner* — Steven Cotroneo
(74) *Attorney, Agent, or Firm* — Stradley Ronon Stevens & Young, LLP

(57) ABSTRACT

Apparatuses and methods of treating a collapsed vertebra may include inserting cannulae into the damaged vertebral body and one or more adjacent vertebral bodies and repositioning the one or more adjacent vertebral bodies by manipulating one or more of the cannulae. Before or after repositioning the vertebral bodies, the method may further include passing through the cannula and into the damaged vertebra a disruption tool for fracturing the damaged vertebral body. Once the cortical bone is broken or otherwise disrupted, the height of the damaged vertebral body may be restored, for example by removing the disruption tool and inserting through the cannula another tool, implant, device and/or material to restore the height of the vertebral body and to restore normal spinal curvature in the affected area. Bone cement, bone chips, demineralized bone or other grafting material or filler may be added with or without an implanted device to augment the damaged vertebral body.

29 Claims, 33 Drawing Sheets

U.S. PATENT DOCUMENTS

| | | | |
|---|---|---|---|
| 6,248,110 | B1 | 6/2001 | Reiley et al. |
| 6,423,083 | B2 | 7/2002 | Reiley et al. |
| 6,648,891 | B2* | 11/2003 | Kim .................. 606/86 B |
| 7,060,066 | B2* | 6/2006 | Zhao et al. .............. 606/279 |
| 2002/0049444 | A1* | 4/2002 | Knox ...................... 606/61 |
| 2002/0068974 | A1 | 6/2002 | Kuslich et al. |
| 2003/0088249 | A1 | 5/2003 | Furderer |
| 2004/0073308 | A1 | 4/2004 | Kuslich et al. |
| 2004/0097930 | A1 | 5/2004 | Justis et al. |
| 2004/0204710 | A1* | 10/2004 | Patel et al. ............... 606/53 |
| 2005/0021040 | A1 | 1/2005 | Bertagnoli ............... 606/90 |
| 2005/0203533 | A1 | 9/2005 | Ferguson et al. ......... 606/90 |
| 2005/0273167 | A1* | 12/2005 | Triplett et al. .......... 623/17.11 |
| 2006/0079905 | A1* | 4/2006 | Beyar et al. ............. 606/76 |
| 2006/0089715 | A1 | 4/2006 | Truckai et al. |
| 2006/0095138 | A1 | 5/2006 | Truckai et al. |
| 2006/0100706 | A1 | 5/2006 | Shadduck et al. |
| 2006/0106459 | A1 | 5/2006 | Truckai et al. |
| 2006/0122625 | A1 | 6/2006 | Truckai et al. |
| 2006/0149268 | A1 | 7/2006 | Truckai et al. |
| 2006/0149278 | A1* | 7/2006 | Abdou ..................... 606/90 |

FOREIGN PATENT DOCUMENTS

| | | |
|---|---|---|
| WO | WO 2004/047689 | 6/2004 |
| WO | WO 2004/086934 | 10/2004 |
| WO | WO 2005/027734 | 3/2005 |

OTHER PUBLICATIONS

Gaitanis et al., "Balloon kyphoplasty for the treatment of pathological vertebral compression fractures," Eur Spine 14:250-260 (2005).

Jang, "Pulmonary embolism of polymethylmethacrylate after percutaneous vertebroplasty: a report of three cases," Spine 27(19):E416-E418 (2002).

Lieberman et al., "Initial outcome and efficacy of kyphoplasty in the treatment of painful osteoporotic vertebral compression fractures," Spine 26(14):1631-1638 (2001).

Magerl et al., "A comprehensive classification of thoracic and lumbar injuries," Eur Spine 184-201 (1994).

Truumees, "Comparing kyphoplasty and vertebroplasty," Advances in Osteoporotic Fracture Management 1(4) (2002).

* cited by examiner

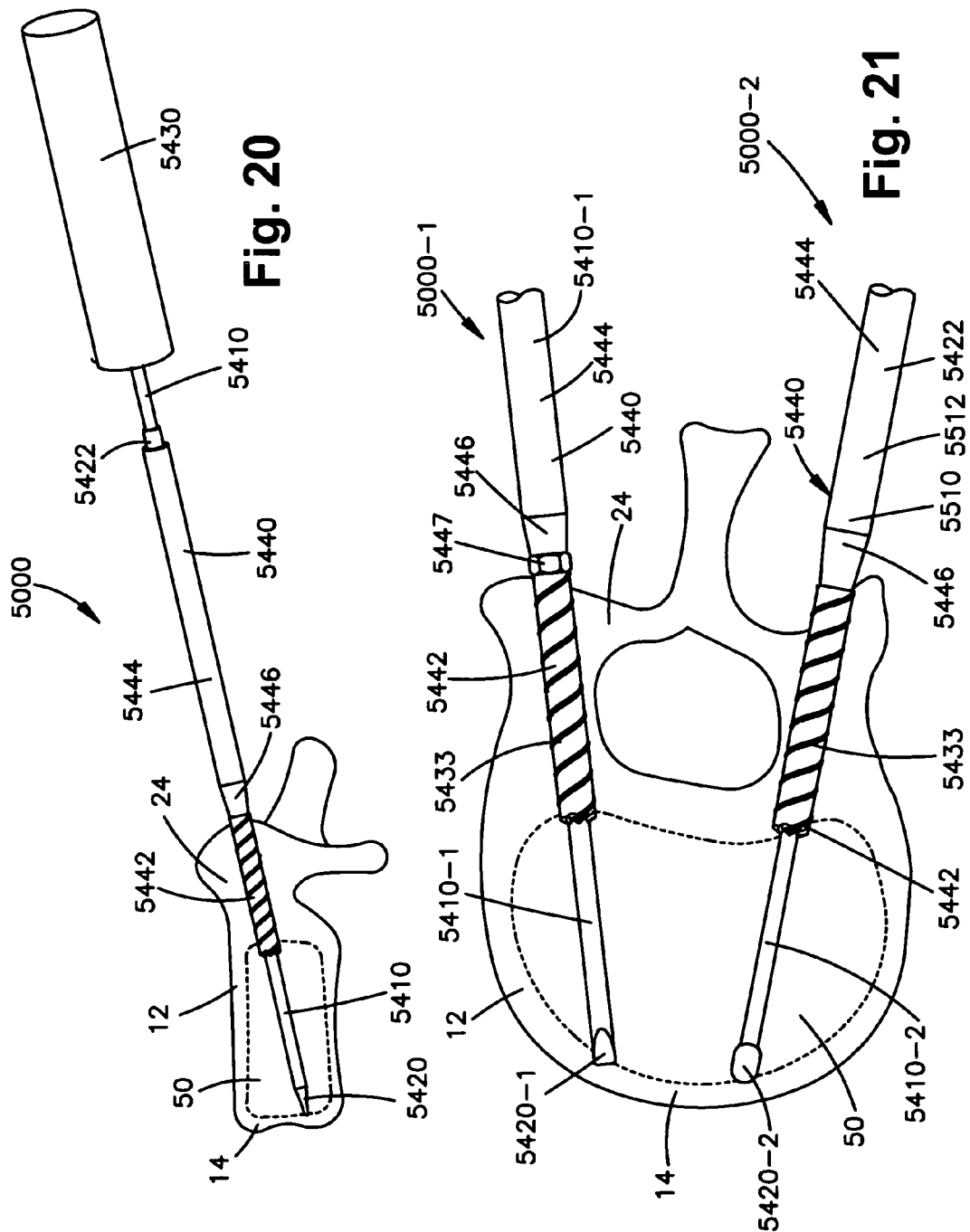

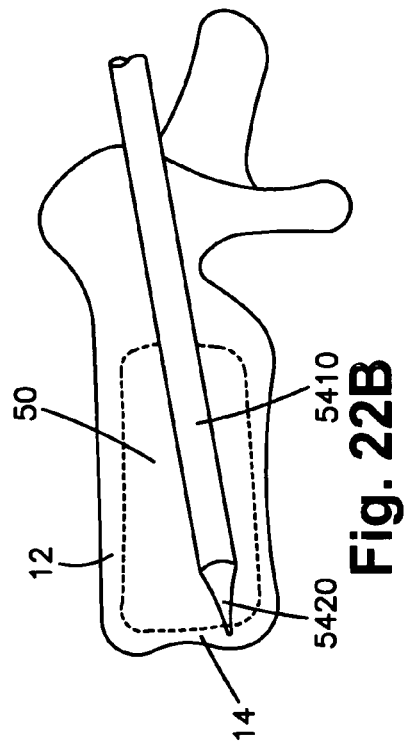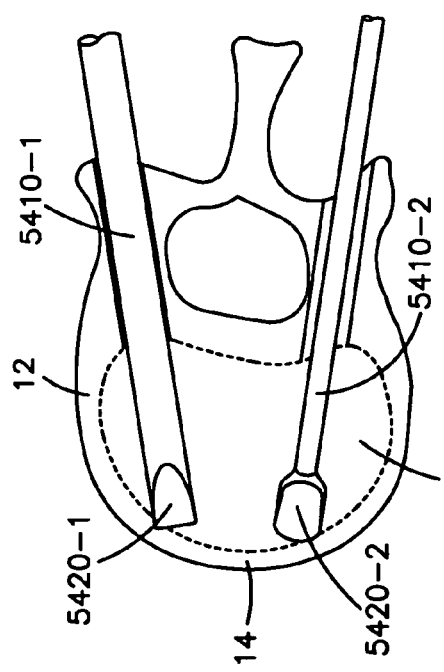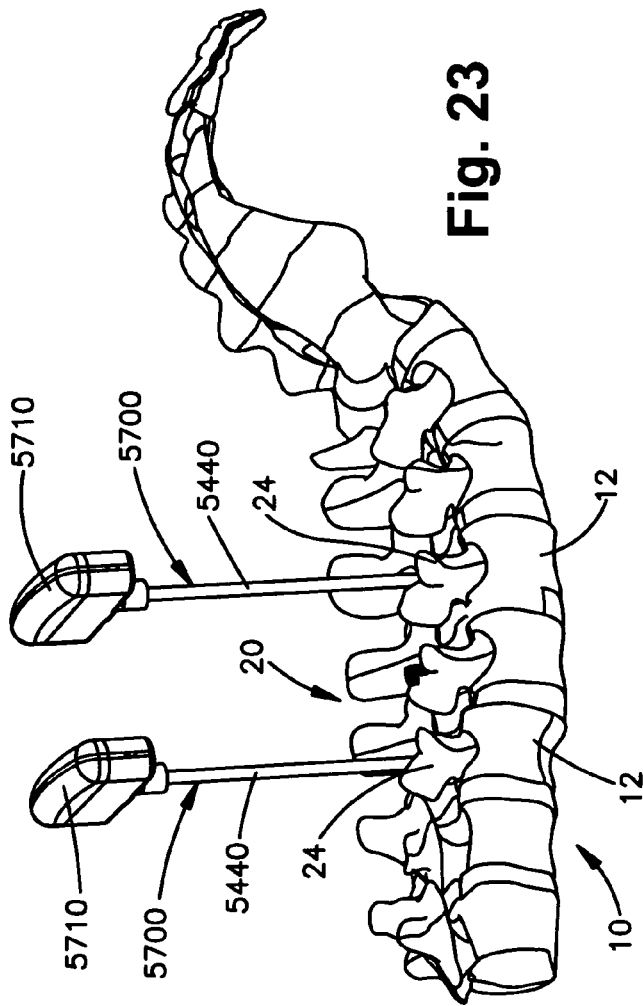

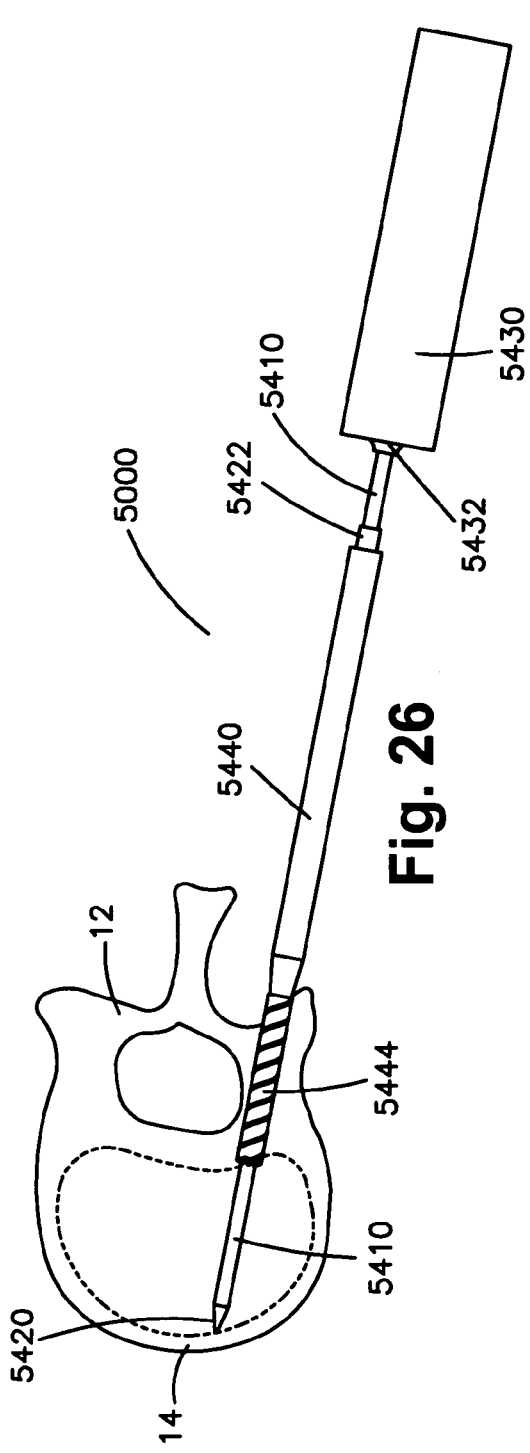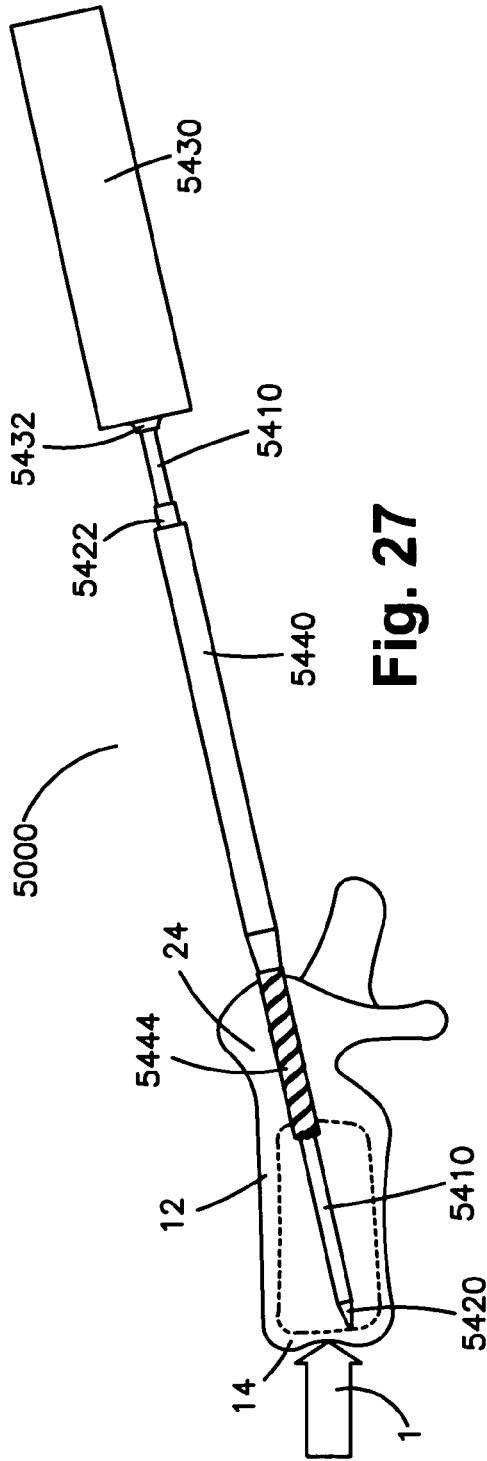

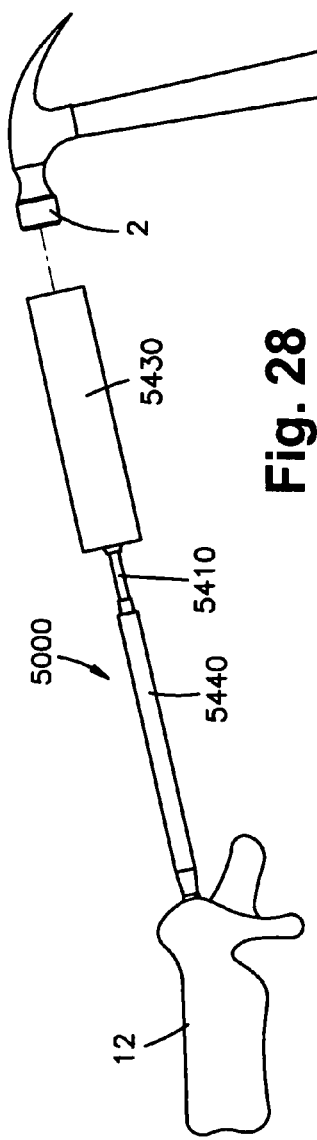
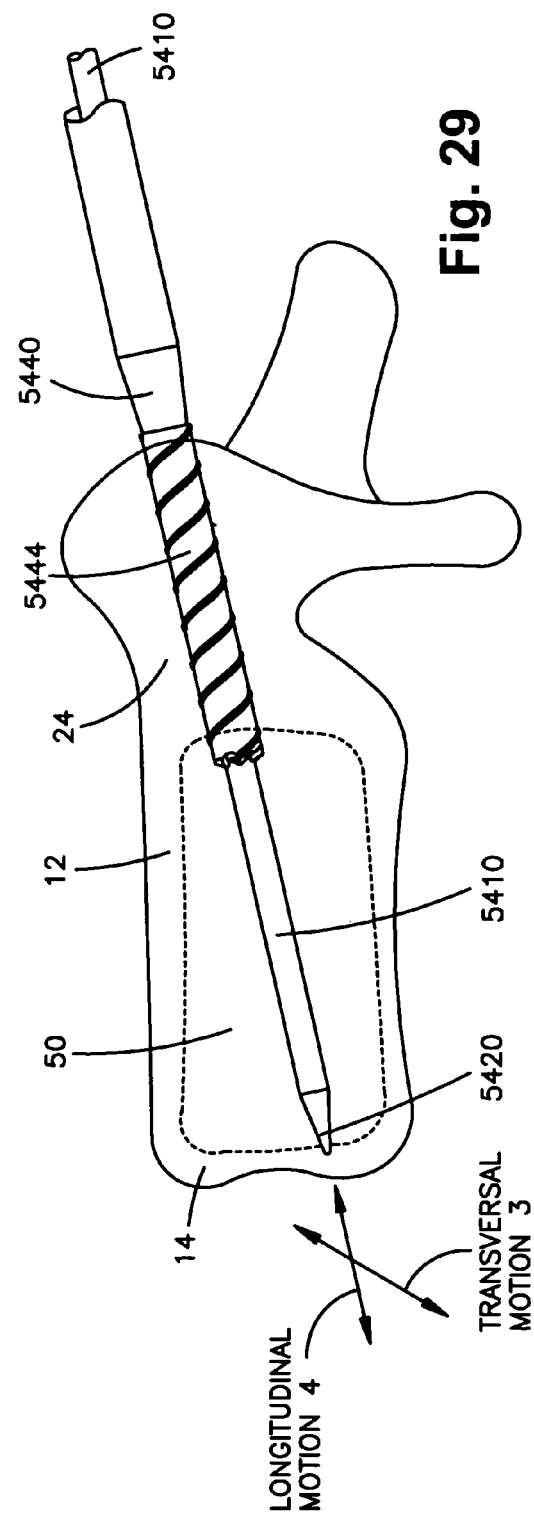

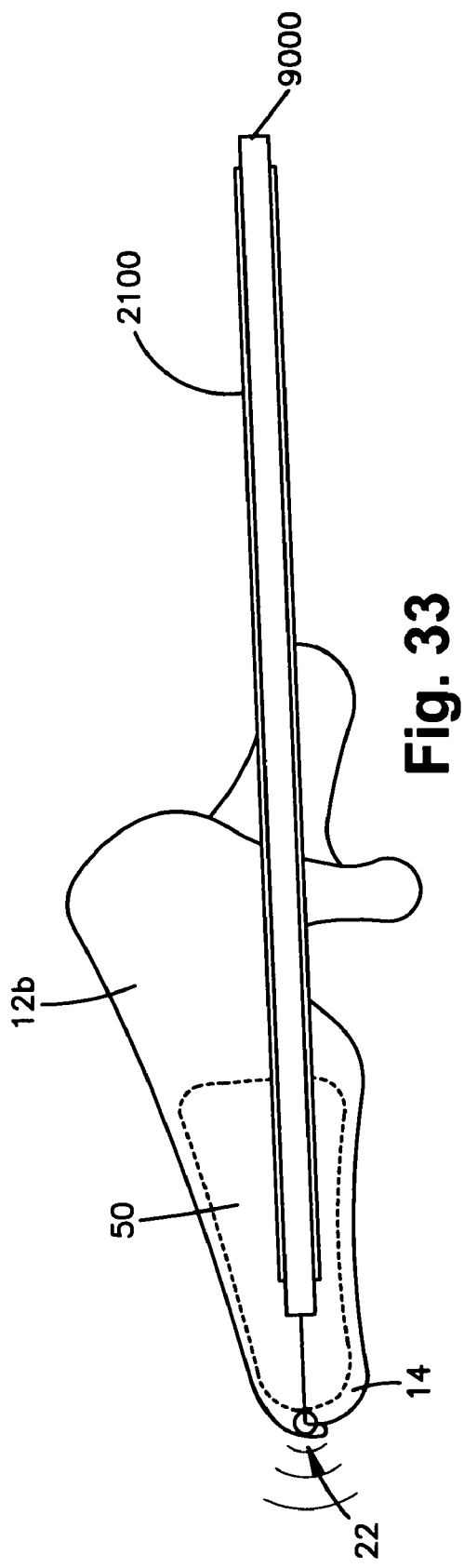
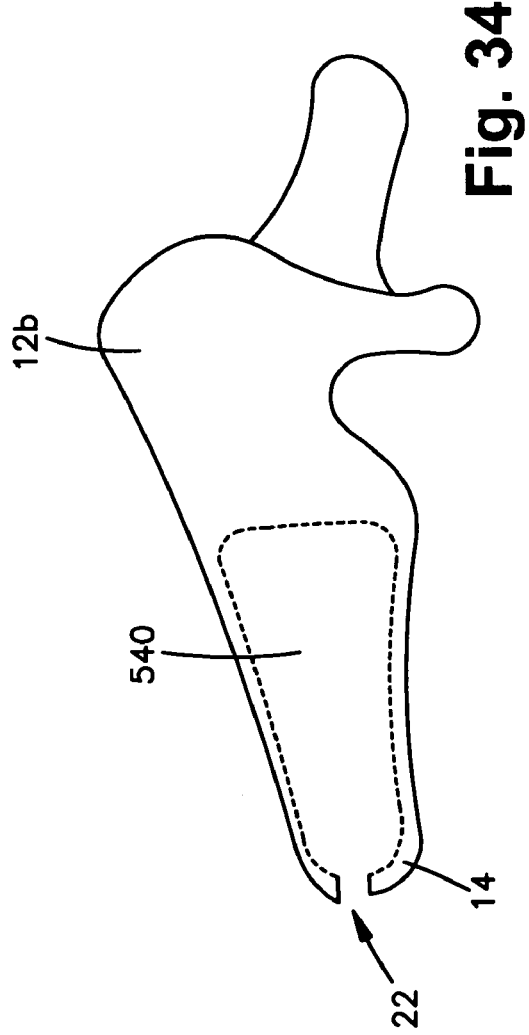

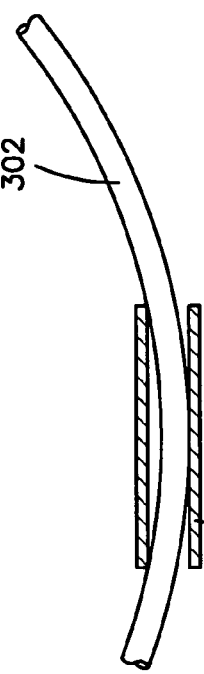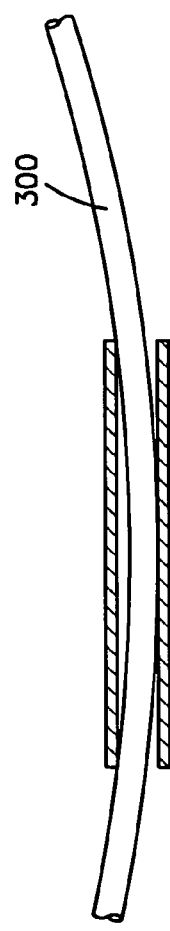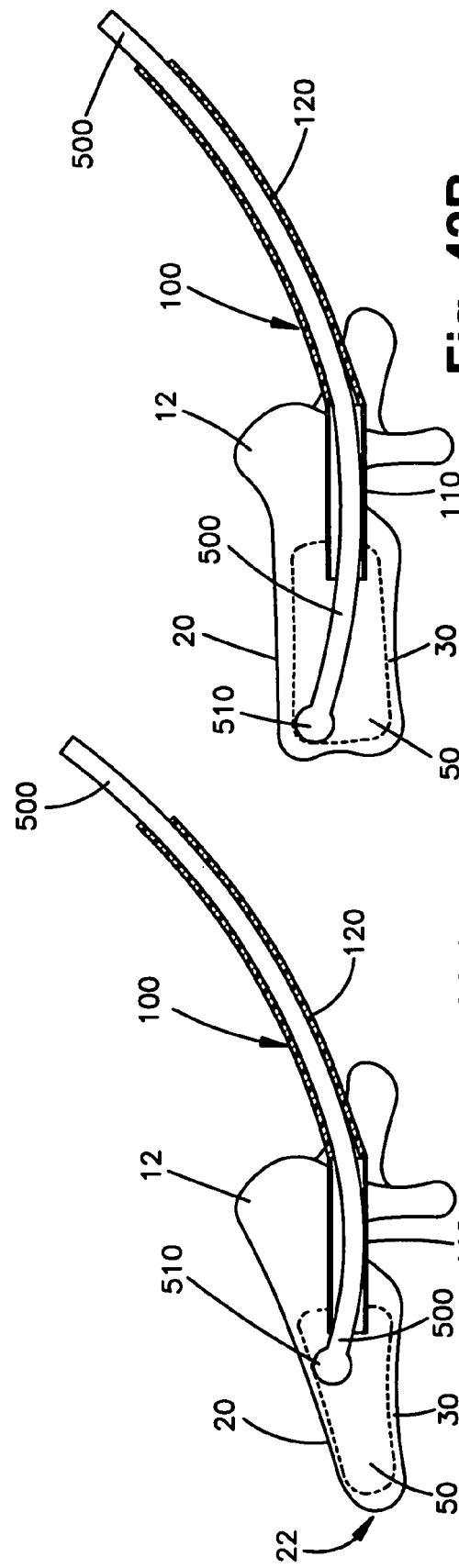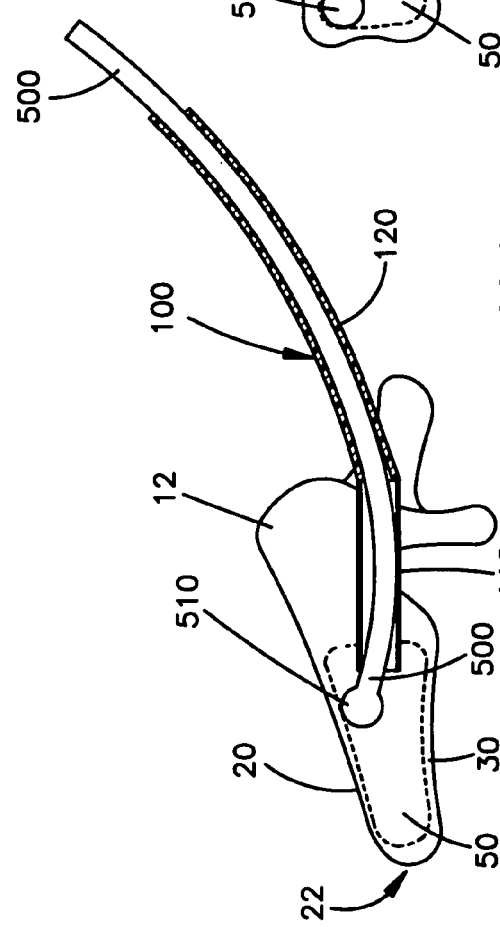

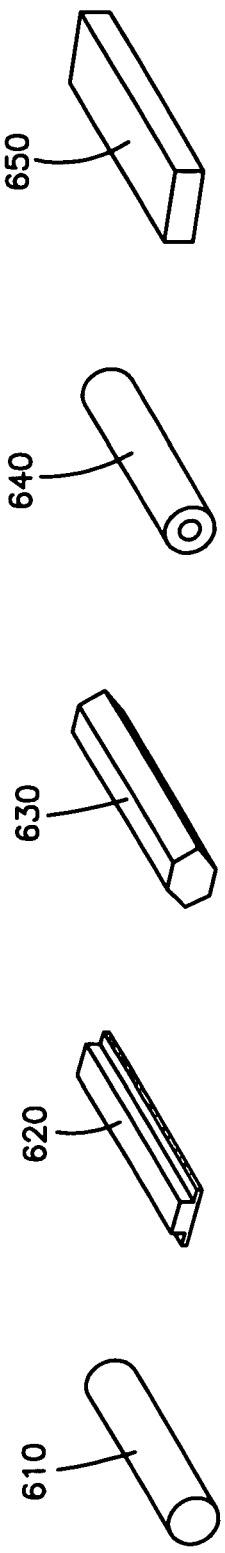
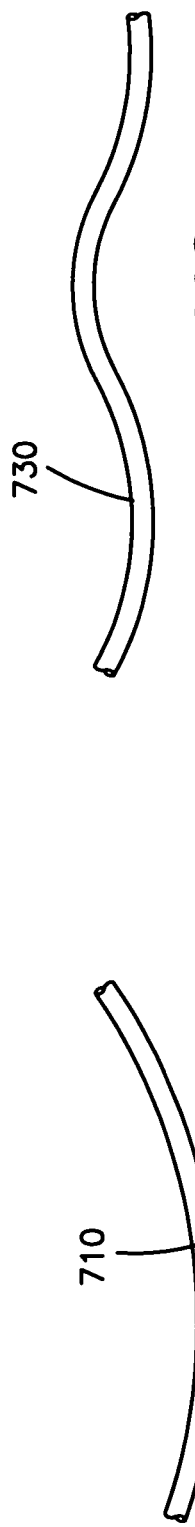

APPARATUS AND METHODS FOR VERTEBRAL AUGMENTATION

CROSS-REFERENCE TO RELATED APPLICATIONS

This application claims priority to U.S. Provisional Application Nos. 60/725,773 filed on Oct. 12, 2005, 60/726,835 filed Oct. 13, 2005, 60/728,442 filed Oct. 19, 2005, 60/730,909 filed Oct. 27, 2005, and 60/733,026 filed Nov. 3, 2005. This application also claims priority to U.S. application Ser. Nos. 11/471,169 filed on Jun. 19, 2006, 11/523,202 filed on Sep. 19, 2006, and 11/527,280 filed on Sep. 25, 2006

FIELD OF THE INVENTION

The invention relates to surgical implants, and more particularly to minimally invasive apparatus and methods for augmenting vertebrae and restoring spinal lordosis.

BACKGROUND OF THE INVENTION

Vertebral compression fractures, as illustrated in FIG. 1, represent a generally common spinal injury and may result in prolonged disability. These fractures involve collapsing of one or more vertebral bodies 12 in the spine 10. Compression fractures of the spine usually occur in the lower vertebrae of the thoracic spine or the upper vertebra of the lumbar spine. They generally involve fracture of the anterior portion 18 of the affected vertebra 12 (as opposed to the posterior side 16). Spinal compression fractures can result in deformation of the normal alignment or curvature, e.g., lordosis, of vertebral bodies in the affected area of the spine. Spinal compression fractures and/or related spinal deformities can result, for example, from metastatic diseases of the spine, from trauma or can be associated with osteoporosis. Until recently, doctors were limited in how they could treat such compression fractures and related deformities. Pain medications, bed rest, bracing or invasive spinal surgery were the only options available.

More recently, minimally invasive surgical procedures for treating vertebral compression fractures have been developed. These procedures generally involve the insertion of a rigid cannula, needle or trocar inserted into the interior of a collapsed or otherwise damaged vertebral body. The cannula may include a lumen or central passage through which another tool, implant or filler material may be passed in order to reposition and/or augment the vertebral body. A common surgical approach to the interior of a vertebral body is from the posterior side, e.g., through one or both pedicles as shown in FIG. 2.

The most basic of these procedures is vertebroplasty, which literally means fixing the vertebral body, and may be done without first repositioning the bone. Briefly, a cannula or special bone needle is passed slowly through the soft tissues of the back. Image guided x-ray, along with a small amount of x-ray dye, allows the position of the needle to be seen at all times. A small amount of polymethylmethacrylate (PMMA) or other orthopedic bone cement is pushed through the needle into the vertebral body. PMMA is a medical grade substance that has been used for many years in a variety of orthopedic procedures. Generally, the cement is mixed with an antibiotic to reduce the risk of infection, and a powder containing barium, tantalum, or iodine solution which allows it to be seen on the X-ray.

Vertebroplasty can be effective in the reduction or elimination of fracture pain, prevention of further collapse, and a return to mobility in patients. However, this procedure may not reposition the fractured bone and therefore may not address the problem of spinal deformity due to the fracture. It generally is not performed except in situations where the kyphosis between adjacent vertebral bodies in the effected area is less than 10 percent. Moreover, this procedure requires high-pressure cement injection using low-viscosity cement, and may lead to cement leaks in 30-80% of procedures, according to recent studies. In most cases, the cement leakage does no harm. In rare cases, however, polymethymethacrylate or other cement leaks into the spinal canal or the perivertebral venous system and causes pulmonary embolism, resulting in death of the patient.

A number of more advanced treatments for vertebral compression fractures are known, and generally involve two phases: (1) reposition, or restoration of the original height of the vertebral body and consequent lordotic correction of the spinal curvature; and (2) augmentation, or addition of material to support or strengthen the fractured bone. As with vertebroplasty, such procedures generally involve use of a cannula, catheter, needle, trocar or other introducer to provide access to the interior of an effected vertebral body.

For example, one such treatment, balloon kyphoplasty (Kyphon, Inc.), is illustrated in FIGS. 3A-D. A catheter having an expandable balloon tip is inserted through a cannula, sheath or other introducer into a central portion of a fractured vertebral body comprising relatively soft cancellous bone surrounded by fractured cortical bone (FIG. 3A). Kyphoplasty then achieves the reconstruction of the lordosis, or normal curvature, by inflating the balloon, which expands within the vertebral body restoring it to its original height (FIG. 3B). The balloon is removed, leaving a void within the vertebral body, and PMMA or other filler material such as, for example, bone cement, is then injected through the cannula into the void (FIG. 3C) as described above with respect to vertebroplasty. The cannula is removed and the cement cures to augment, fill or fix the bone (FIG. 3D).

Disadvantages of this procedure include the high cost, the loss in height of the vertebral body after the removal of the balloon catheter, the high pressures required to impart sufficient force to separate or maintain the separation of the vertebral endplates, and the possible perforation of the vertebral endplates during the procedure. As with vertebroplasty, perhaps the most feared, albeit remote, complications related to kyphoplasty are related to leakage of bone cement. For example, a neurologic deficit may occur through leakage of bone cement into the spinal canal. Such a cement leak may occur through the low resistance veins of the vertebral body or through a crack in the bone which has not been appreciated previously. Other complications include; additional adjacent level vertebral fractures, infection and cement embolization. Cement embolization occurs by a similar mechanism to a cement leak. The cement may be forced into the low resistance venous system and travel to the lungs or brain resulting in a pulmonary embolism or stroke. Additional details regarding balloon kyphoplasty may be found, for example, in U.S. Pat. Nos. 6,423,083, 6,248,110, and 6,235,043 to Riley et al., each of which is incorporated by reference herein in its entirety.

Another procedure for treating vertebral compression fractures is the Optimesh system (Spineology, Inc., Stillwater, Minn.), which provides minimally invasive delivery of a cement or allograft or autograft bone using an expandable mesh bag, or containment device, within the involved vertebral body. The bag or graft remains inside the vertebral body after its inflation, which prevents an intraoperative loss of reposition, such as can occur during a kyphoplasty procedure when the balloon is withdrawn. The optimesh system may also prevent leakage of the cement or bone material which is captured or contained by the bag. One drawback of this system, however, is that the mesh implant is not well integrated in the vertebral body. This can lead to relative motion between the implant and vertebral body, and consequently to a post-operative loss of reposition. The system is also complex and relatively expensive. Additional details regarding this procedure may be found, for example, in published U.S. Patent Publication No. 20040073308, which is incorporated by reference herein in its entirety.

Still another procedure used in the treatment of vertebral compression fractures is an inflatable polymer augmentation mass known as a SKy Bone Expander. This device can be expanded up to a pre-designed size and Cubic or Trapezoid configuration in a controlled manner. Like the Kyphon balloon, once optimal vertebra height and void are achieved, the SKy Bone Expander is removed and PMMA cement or other filler is injected into the void. This procedure therefore entails many of the same drawbacks and deficiencies described above with respect to kyphoplasty.

Thus, a common drawback of most known systems and procedures for repositioning and augmenting damaged vertebrae is that they involve the use of relatively complex apparatus introduced through rigid introducers. The rigid introducers can damage the vertebral pedicles and/or surrounding tissues during insertion and/or manipulation of the augmentation apparatus. Accordingly, there remains a need in the art to provide safe and effective apparatus and methods for minimally invasive repositioning of and osteopathic augmentation of vertebral bodies to restore lordosis of the spine.

Regardless of the type of implant or augmentation method used, however, any such treatment of a collapsed or otherwise fractured vertebral body generally must be performed within about six weeks of the injury. Otherwise, the fractured bones may tend to heal in their collapsed state, making it difficult or impossible to reposition the affected vertebral bodies and/or restore lordosis without first disrupting, or breaking up, the improperly healed fracture. Moreover, because of the generally close proximity of nerves, blood vessels and other sensitive soft tissues to the spine, any method for disrupting the affected area of a collapsed vertebral body should be minimally invasive and controlled to avoid damaging such surrounding tissues. Accordingly, there remains a need in the art for suitable tools or methods to safely and effectively disrupt such improperly healed bones in a minimally invasive way.

SUMMARY OF THE INVENTION

The present invention provides apparatus and methods for minimally invasive vertebral augmentation and restoration of spinal lordosis. In one embodiment, a cannula comprises a rigid member having a rigid member lumen dimensioned to pass an instrument, and a flexible member having a flexible member lumen. The flexible member is coupled to the rigid member such that the lumen of the rigid member and the lumen of the flexible member form a passage through which an instrument may pass.

In another embodiment, an instrument used for correction of the spine comprises at least two body segments, each body segment having a distal end and a proximal end, at least one joint connecting the distal end of a first body segment to the proximal end of an adjacent body segment, the joints permitting the body segments to articulate with respect to each other. The instrument further includes an elongated flexible element attached to the distal end of one body segment, the elongated element extending the length of the at least two body segments. When the elongated element is pulled towards the proximal end of the body segment, the distal body segment articulates with respect to the adjacent body segment.

In a further embodiment an apparatus for repositioning vertebrae comprises at least one elongated member, each of the elongated members having a first end and a second end, where the first end of each elongated member is configured for insertion into a vertebral body. The apparatus further includes a fixation rod having an arcuate shape, and at least one clamp configured to adjustably secure the second end of one of the elongated members to the fixation rod. The clamp is configured to move along the fixation rod to pivot the elongated member to reposition a vertebral body.

The present invention also provides for bent instruments and implants that may be passed through the cannulae of the present invention and into a bone or other body parts, for example a damaged vertebra. Such implants may be used, for example, to reposition endplates of a damaged vertebral body and/or to augment a vertebral body.

The cannulae and/or bent instruments of the present invention may be used in conjunction with other apparatus and methods. For example, after repositioning a vertebral body using a bent instrument applied through a partially flexible cannula, one or more implants may be inserted into the vertebral body to further augment the vertebral body. One or more other instruments or apparatus may also be used, for example an external fixation apparatus to aid in repositioning vertebrae adjacent to a collapsed vertebra, e.g., to reduce compressive forces on the vertebra.

The cannulae and/or repositioning rods of the present invention may be comprised of any biocompatible material having desired characteristics, for example a biocompatible polymer, metal, ceramic, Nitinol, PEEK, composite or any combination thereof. In some embodiments, the cannulae and/or repositioning rods or other implants or instruments may be resorbable.

In some embodiments, a method for treating a damaged vertebral body, comprises the steps of restoring spinal lordosis in a region of a damaged vertebral body, fracturing the damaged vertebral body, restoring a height of the damaged vertebral body, and augmenting the vertebral body.

In another embodiment, a kit comprises various combinations of assemblies and components. A kit may include, for example, a cannula according to the present invention and one or more instruments and/or implants for restoring vertebral height and/or for augmenting a vertebral body. For example, a kit may include a cannula having a rigid member and a flexible member coupled with a rigid member, and a curved instrument for restoring the height of a vertebral body. Other kits may include another implant instead of or in addition to the curved instrument. In other embodiments, a kit may include a cannula, an external fixation or tensioning member and/or a longitudinal fixation member. Such embodiments may also comprise a syringe or other apparatus for injecting a cement or other filler into a vertebral body.

BRIEF DESCRIPTION OF THE DRAWINGS

The invention and further developments and features of the invention are explained in even greater detail in the following exemplary drawings. The present invention can be better understood by reference to the following drawings, wherein like references numerals represent like elements. The drawings are merely exemplary to illustrate certain features that may be used singularly or in combination with other features and the present invention should not be limited to the embodiments shown.

FIG. 20 is a side view of a disruption device inserted into a vertebra according to an embodiment of the present invention;

FIG. 21 is a top view of two disruption devices inserted into a vertebra according to an embodiment of the present invention;

FIG. 22A is close up top view of the disruption devices and the vertebra of FIG. 16;

FIG. 22B is a close up side view of the disruption devices and the vertebra of FIG. 21;

FIG. 23 is a perspective view of a spine showing the insertion of cannulae into vertebra from the posterior aspect of the spine;

FIG. 26 is top view of a disruption device inserted into a vertebra according to an embodiment of the present invention;

FIG. 27 is a side view of a disruption device inserted into a vertebra according to an embodiment of the present invention;

FIG. 28 is a schematic side view of a striking instrument and two disruption devices inserted into a vertebra according to embodiments of the present invention;

FIG. 29 is a side view of a disruption device inserted into a vertebra, showing axes of motion according to an embodiment of the present invention;

FIG. 33 is a schematic side view illustration of a device and method for disrupting a fractured vertebral body;

FIG. 34 is a schematic side view illustration of a fractured vertebral body;

FIGS. 41A and 41B are schematic cross-sectional side views of a rigid member of a cannula and a rod according to an embodiment of the present invention;

FIGS. 42A and 42B are schematic cross-sectional side views of a cannula and a rod in use in a vertebra according to an embodiment of the present invention;

FIG. 43 is a perspective view illustration showing various shapes of instruments or implants that may be used according to embodiments of the present invention;

FIG. 44 is a side view schematic illustration showing various curvatures of instruments or implants that may be used according to embodiments of the present invention;

DETAILED DESCRIPTION

Figure 1:
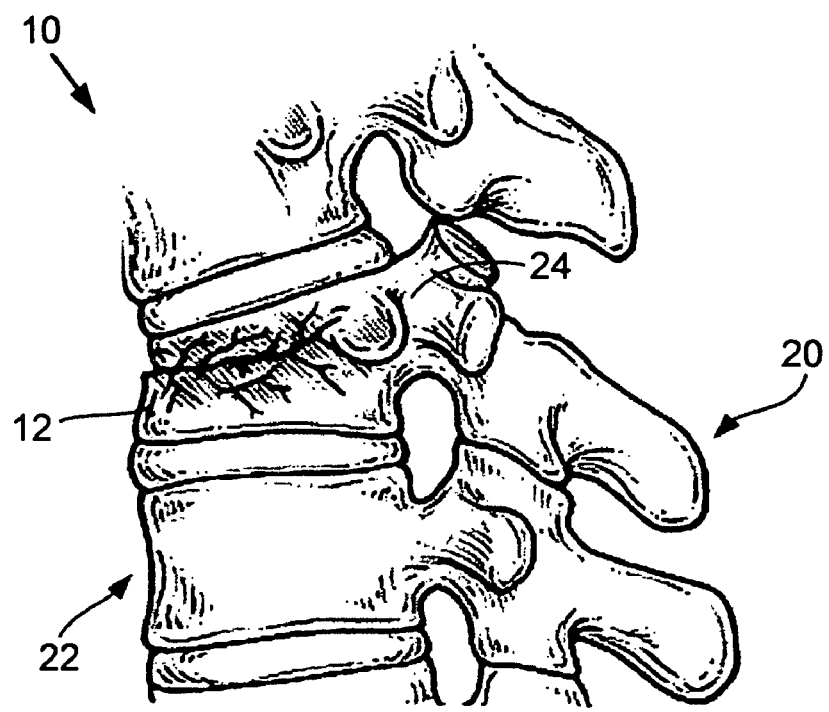
FIG. 1 is an illustration of a spine having a vertical compression fracture in one vertebral body.
Figure 2:
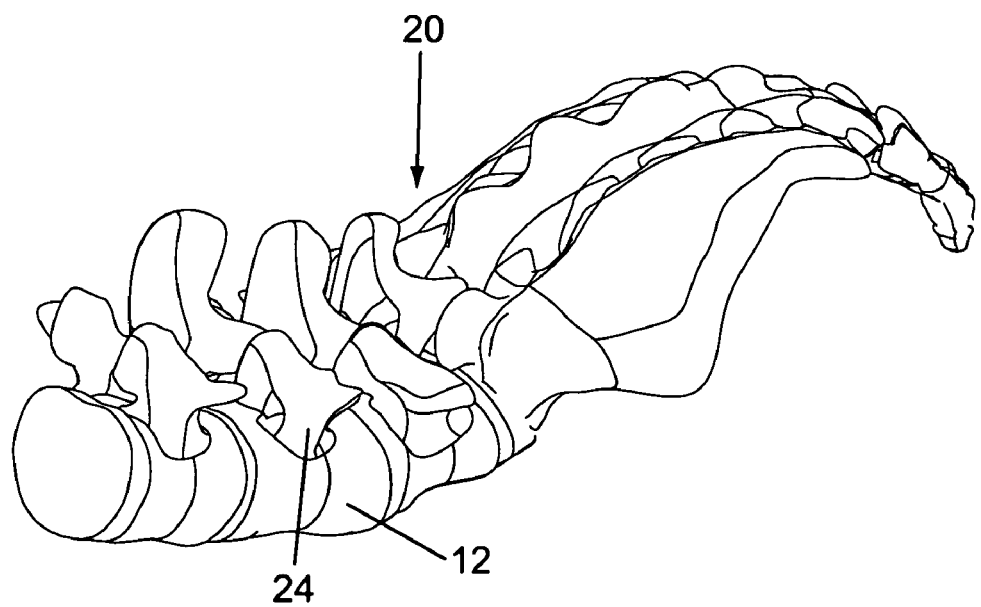
FIG. 2 is an illustration of a spine showing a posterior surgical approach through a vertebral pedicle.
Figure 3A:
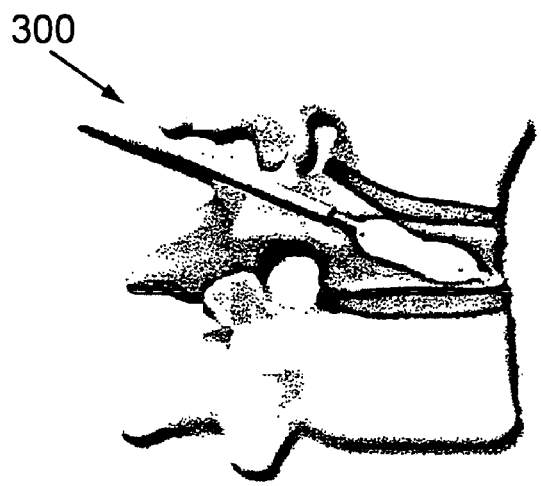
FIGS. 3A-D are illustrations of a prior art method for treating a vertical compression fracture.
Figure 3B:
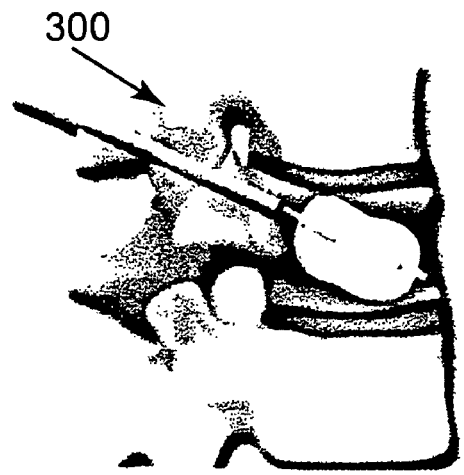
Figure 3C:
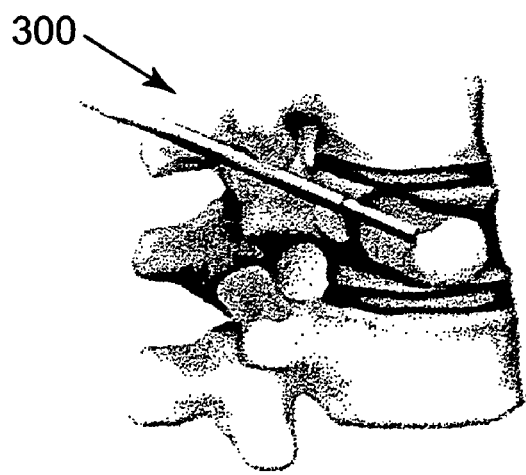
Figure 3D:
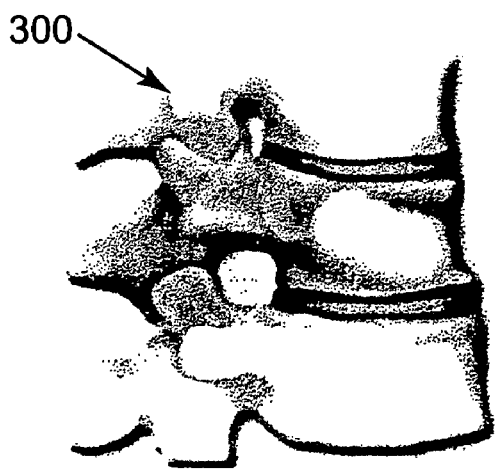
Figure 4:
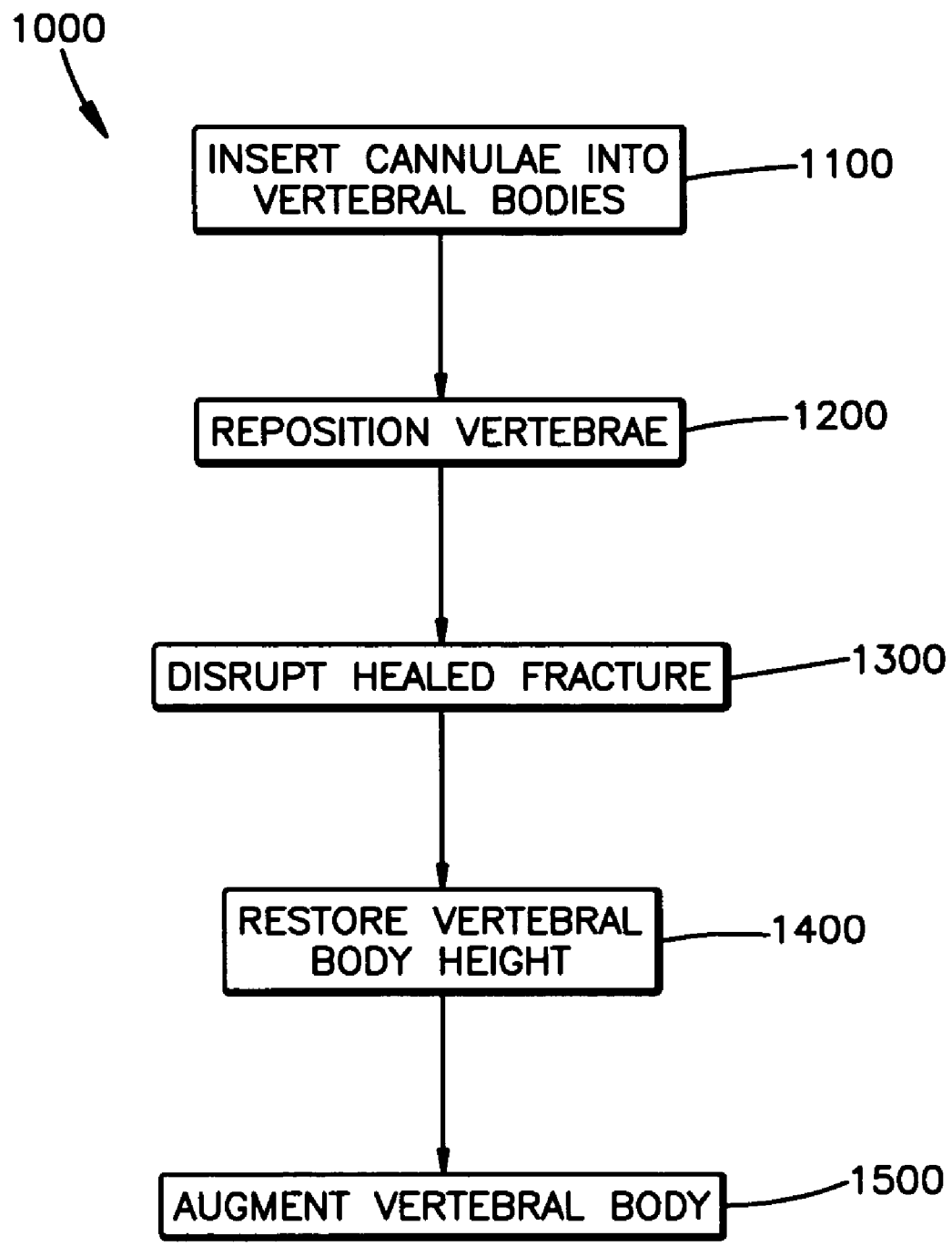
FIG. 4 is a flow chart of a method for restoring lordosis and augmenting a vertebral body according to an embodiment of the present invention.

A method 1000 of restoring spinal lordosis and augmenting a vertebral body, for example to treat a vertebral compression fracture will be described (see FIG. 4). In general, method 1000 may include one or more of the following steps: step 1100, inserting one or more cannulae into a damaged vertebral body and/or into vertebral bodies adjacent to the damaged vertebral body. Step 1100 may be performed from a posterior approach. Step 1200 involves repositioning the vertebrae using the cannulae. Step 1200 may be performed in conjunction with an external fixation device. Step 1300, disrupts fractured bone in the damaged vertebra. Step 1400, restores the vertebral body height; and step 1500 augments the restored vertebral body, for example using an implant or filler material. Some or all of the steps 1100, 1200, 1300, 1400 and/or 1500 of method 1000 may be performed in an order as shown in FIG. 4, or in any other order, and may be used in combination with other methods. Additional details and examples regarding each of the steps 1100, 1200, 1300, 1400 and 1500 of method 1000 are described in more detail below.

Insertion of Cannulae (Step 1100)

Figure 7:
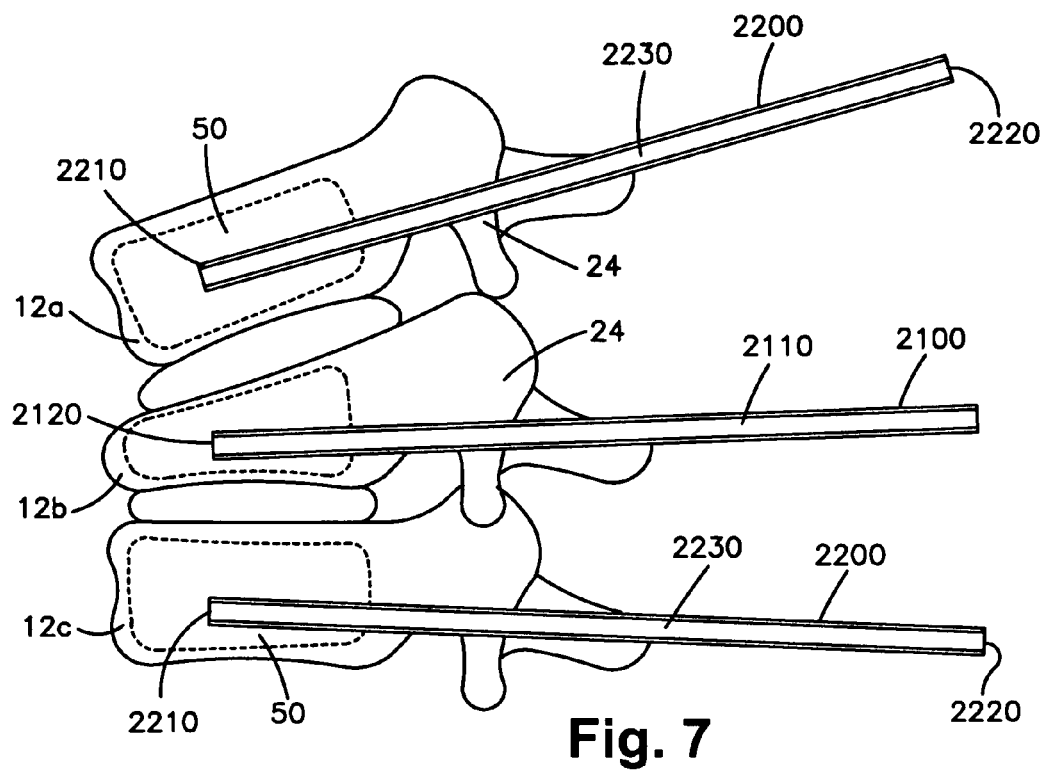
FIG. 7 is a schematic side view illustration of a cannulae inserted into vertebral bodies according to a method of the present invention.

FIG. 7 shows insertion of a cannula 2100 into a damaged vertebrae 12b. Different elongated members 2200, being the same or similar to cannula 100 described later, may be used, for example in step 1100 of FIG. 4. For example, a cannula 2100 may be inserted into a fractured or otherwise damaged vertebral body 12b, and one or more members 2200 may be inserted into or otherwise attached to vertebrae 12a and 12c, which may be above and/or below the damaged vertebral body 12b. One or more of the elongated members 2200 may be a cannula.

Dimensions of the one or more members 2200 and/or cannula 2100 may be the same or different, and may have a diameter, for example, between about 2 and 10 mm. Elongated member 2200 and/or cannula 2100 may be dimensioned to extend out of the vertebra and surrounding soft tissue and may have any desired length, for example between about 10 and about 30 cm, or longer. Elongated member 2200 may comprise stainless steel, a metal, a metal alloy, a polymer, a composite, a ceramic or a combination thereof.

Elongated member 2200 and cannula 2100 may be configured and dimensioned for insertion into a vertebra, e.g., into a central portion 50 of a vertebral body 12 from a posterior approach through a pedicle 24. When inserted, elongated member 2200 and cannula 2100 extend out of the vertebrae 12, through the soft tissue covering the spine 10 and to the outside of the patient. In some embodiments, each elongated member 2200 and/or cannula 2100 may be inserted into a vertebral body through a hole that may be formed through the outer cortical bone of vertebra 12, e.g., through pedicle 24, e.g. by a drill, trocar, or other instrument. In some embodiments, elongated members 2200 may include external threads (not shown) on the outside surface which engage vertebral bodies 12a and 12c to secure elongated members 2200 therein. External threads may run along a distal portion 2210 of elongated member 2200, the entire length of elongated member 2200, or along any desire portion of elongated member 2200. A handle (not shown) may be attached to the proximal end 2220 of the elongated member 2200 and used to manipulate and/or insert members 2200 through pedicles 24.

Elongated member 2200 and cannula 2100 may be dimensioned to extend out of the vertebra and surrounding soft tissue. Member 2200 may be a cannula such as, for example, cannula 2100, or may be another type of cannula, trocar rod, introducer, wire, pin or other device suitable for attaching to or engaging with vertebrae 12 and imparting forces to reposition the vertebrae. Cannula 2100 and/or elongated member 2200 may be cylindrical or any other shape, may include a lumen 2110 and 2230, respectively, to provide access through which tools, implants, fillers or other materials or devices may be inserted into vertebral body 12. Elongated member 2200 may be solid or hollow and may be semi-rigid or substantially rigid, for example in order to impart a torque or other force on a vertebra to which elongated member 2220 is attached.

Refer to the discussion of cannula 100 for additional details of cannula 2100 and/or elongated members 2200.

Reposition Vertebrae (Step 1200)

Figure 5:
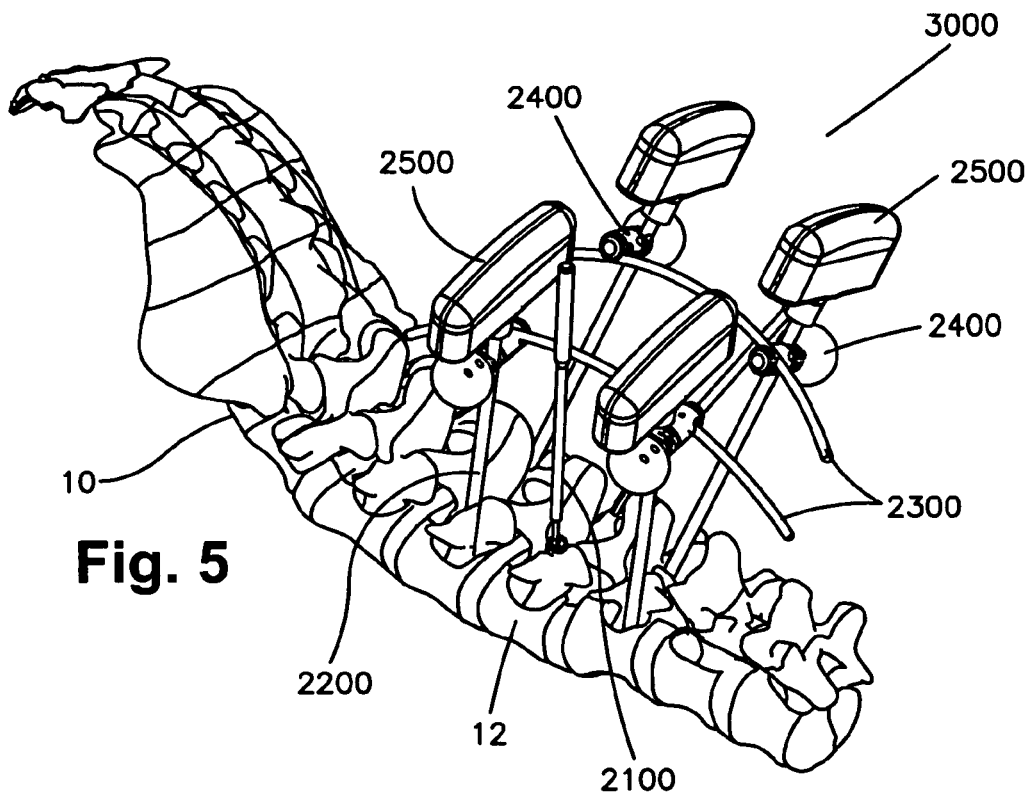
FIG. 5 is a perspective view of an external fixation device in use in a spine according to an embodiment of the present invention.
Figure 6:
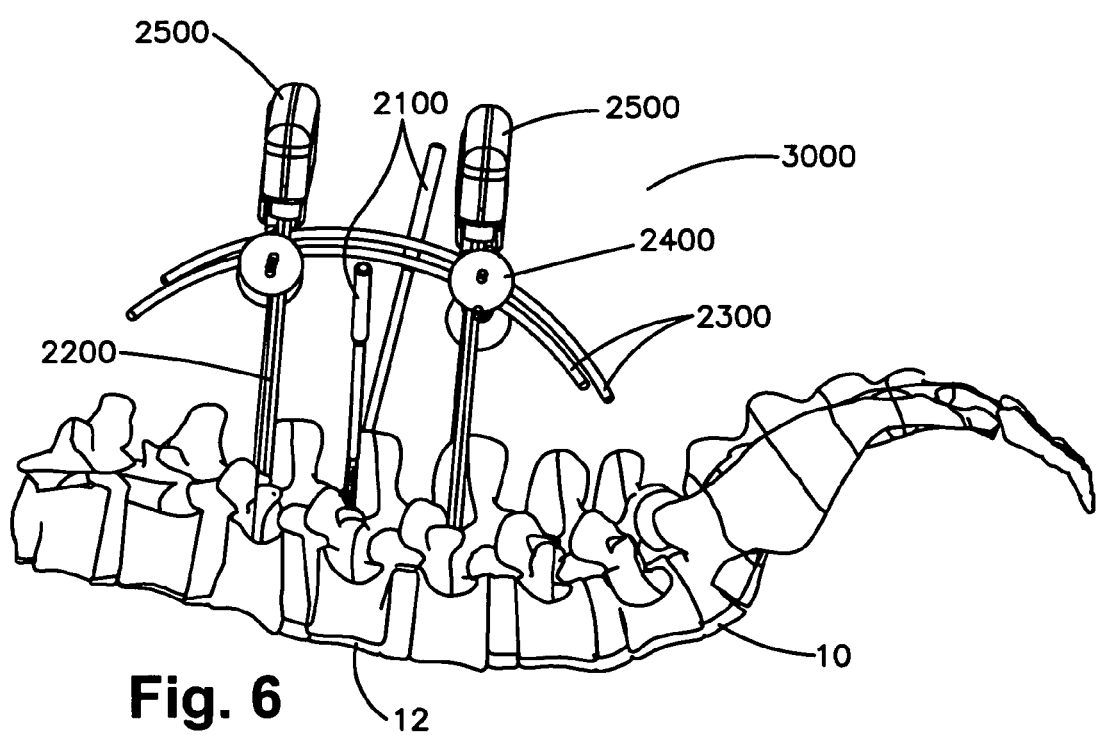
FIG. 6 is a side view of the external fixation device of FIG. 5.

In step 1200 a fixation device may be used to aid in repositioning a vertebra. FIGS. 5 and 6 show a fixation device 3000 for positioning, fixing and/or stabilizing of bones, such as vertebrae 12 of a spine 10. Device 3000 may be used, for example, to impart forces upon vertebral bodies 12 to reposition the bodies 12 and correct lordosis of the spine 10, for example in a region of a fractured vertebral body 12. Fixation device 3000 may have application in other areas of the skeletal structures to reposition damaged or diseased bones.

Device 3000 may comprise one or more elongated members 2200, one or more longitudinal (fixation) members 2300 and one or more clamps 2400 for securing elongated members 2200 to fixation members 2300. In some embodiments, a hole 60 may be formed through the outer cortical bone of vertebra 12, e.g., thorough pedicle 24, e.g. by a drill, trocar, or other instrument. A handle 2500 may be attached to the proximal end of the elongated member 2200 and used to manipulate member 2200 and/or insert members 2200 through pedicles 24.

Optionally, one or more cannulae 2100 may be incorporated within, attached to, or used in conjunction with device 3000. For example, a cannula 2100 may be inserted into a fractured or otherwise damaged vertebral body 12, and one or more members 2200 may be inserted into or otherwise attached to vertebrae 12 above and/or below the damaged vertebral body 12. Members 2200 may be used as cement injection cannulae to prophylactically perform vertebroplasty in vertebrae above and/or below and thus strengthen vertebral bone structure. Furthermore, cement injection into vertebral body above and/or below the damaged vertebra and cement within cannulae may enhance mechanical properties of a segment when later performing repositioning using external forces.

Longitudinal member 2300 may be arcuate, and may have a radius of curvature that approximately corresponds with the distance between an entry point of member 2200 into a vertebral body and the handles 2500 of members 2200. Longitudinal member 2300 may also have any desired length and curvature.

One or more clamps 2400 may secure each elongated member 2200 to longitudinal member 2300. Each clamp 2400 may be adjustable with respect to elongated member 2200 and/or longitudinal member 2300, for example to secure member 2200 to longitudinal member 2300 in any desired orientation. With one end of each elongated member 2200 inserted into or otherwise attached to vertebral bodies 12, and other end of each member 2200 secured by clamp 2400 to longitudinal member 2300, the position of members 2200 may be stabilized or fixed with respect to each other.

FIG. 7 shows members 2200, which may or may not be cannulae, inserted into vertebral bodies 12a and 12c. A distal end 2210 of each member 2200 may be inserted, for example, into a central portion 50 of vertebral bodies 12a and 12c. Members 2200 may have a lumen 2230, for example through which cement, bone chips, or other filler may be inserted into vertebral bodies 12a and 12c. Such cement, bone chips or other filler may be used, for example, to help secure members 2200 within vertebral bodies 12a and 12c.

Also shown in FIG. 7 is a cannula 2100 having a distal end 2120 that is inserted into a collapsed vertebral body 12b. Cannula may include a lumen 2110 through which a tool, implant, cement, bone chips or other filler may be passed and inserted into vertebral body 12b, for example to augment and/or stabilize the damaged vertebral body. Elongated members 2200 may be inserted into one or more vertebrae 12a and 12c, which may be adjacent to damaged vertebra 12b, as shown in FIG. 7.

Figure 8:
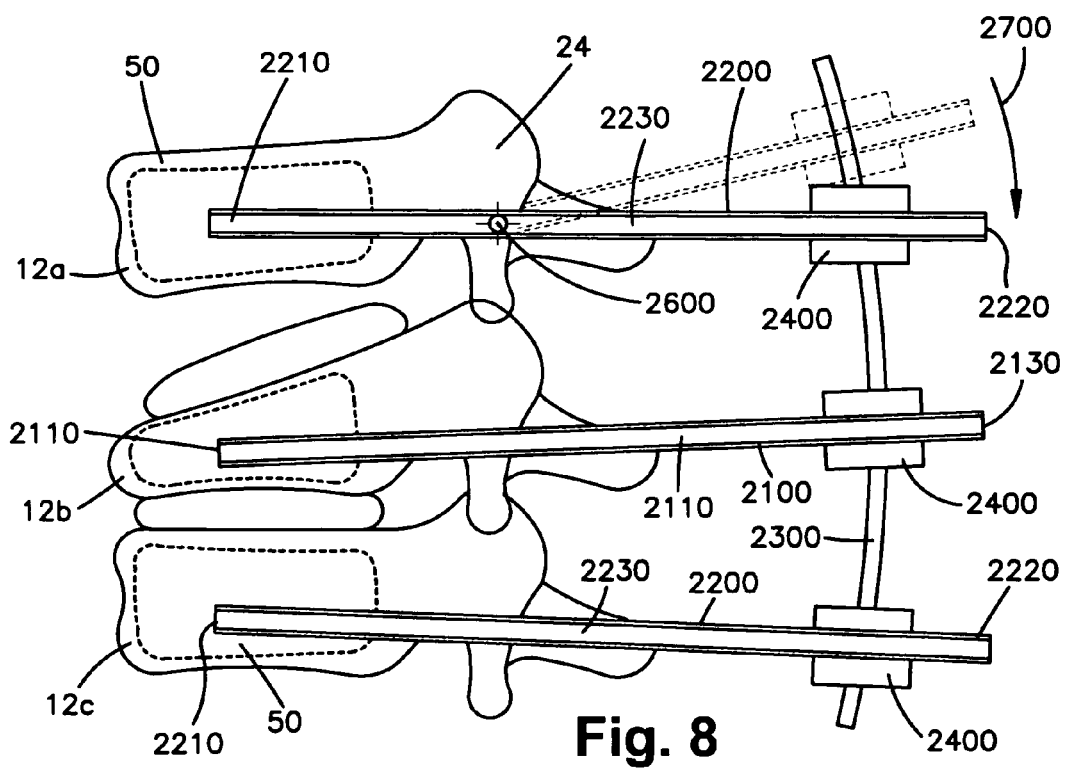
FIG. 8 is a schematic side view illustration of the cannulae of FIG. 7 in use to reposition vertebral bodies.

FIG. 8 shows a method of repositioning vertebral bodies 12a-c, for example to restore normal curvature, or lordosis, in the area of the damaged vertebra 12b prior to augmenting or stabilizing the fractured vertebral body 12b. Distal end 2220 of members 2200 may be adjustably engaged with fixation member 2300, for example using clamps 2400, thereby allowing members 2200 to be fixed with respect to each other or to be repositioned. End 2130 of cannula 2100 may also be attached to fixation member 2300, for example by a clamp 2400 to stabilize and fix the position of vertebrae 12b during repositioning of vertebrae 12a. End 2220 of elongated member 2200 secured to vertebra 12a may be translated along longitudinal member 2300 for example in a direction shown by arrow 2700. Such translation may cause elongated member 2200 to pivot about center of rotation 2600 and impart a moment or torque on vertebral body that may tend to reposition vertebral body 12a, for example to restore normal lordosis of the spine 10.

Figure 14:
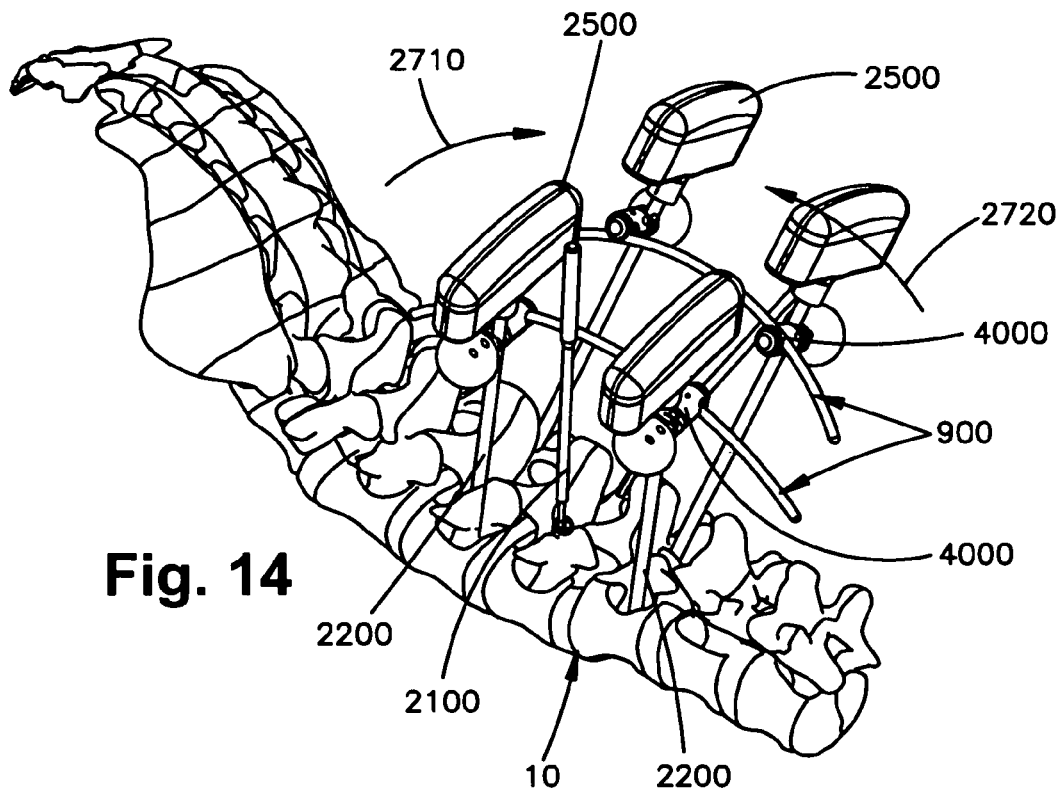
FIG. 14 is a perspective view of a fixation device including the clamp and fixation rod of FIG. 11.

Repositioning of a vertebral body 12a or 12c, for example, adjacent to a fractured vertebral body 12b may reduce compressive forces on vertebra 12b and aid augmentation or restoration of vertebral height, for example using tools, implants, fillers, etc. In other embodiments, a different rotational or translational force may be applied to vertebral bodies using one or more members 2200. For example, member 2200 may be pushed or pulled transversely with respect to spine 10, e.g., instead of or in addition to rotation about pivot 2600, in order to orient or position one or more vertebral bodies 12 into a desired alignment. In some embodiments, cannula 2100 is not secured to fixation member 2300. FIG. 14 shows a perspective view of a fixation device including the clamp and fixation rod of FIG. 11 when a force is applied to elongated members in vertebrae 12a, 12c in different directions along fixation rod to temporarily restore vertebral alignment to facilitate restoration of vertebrae 12b.

Figure 9:
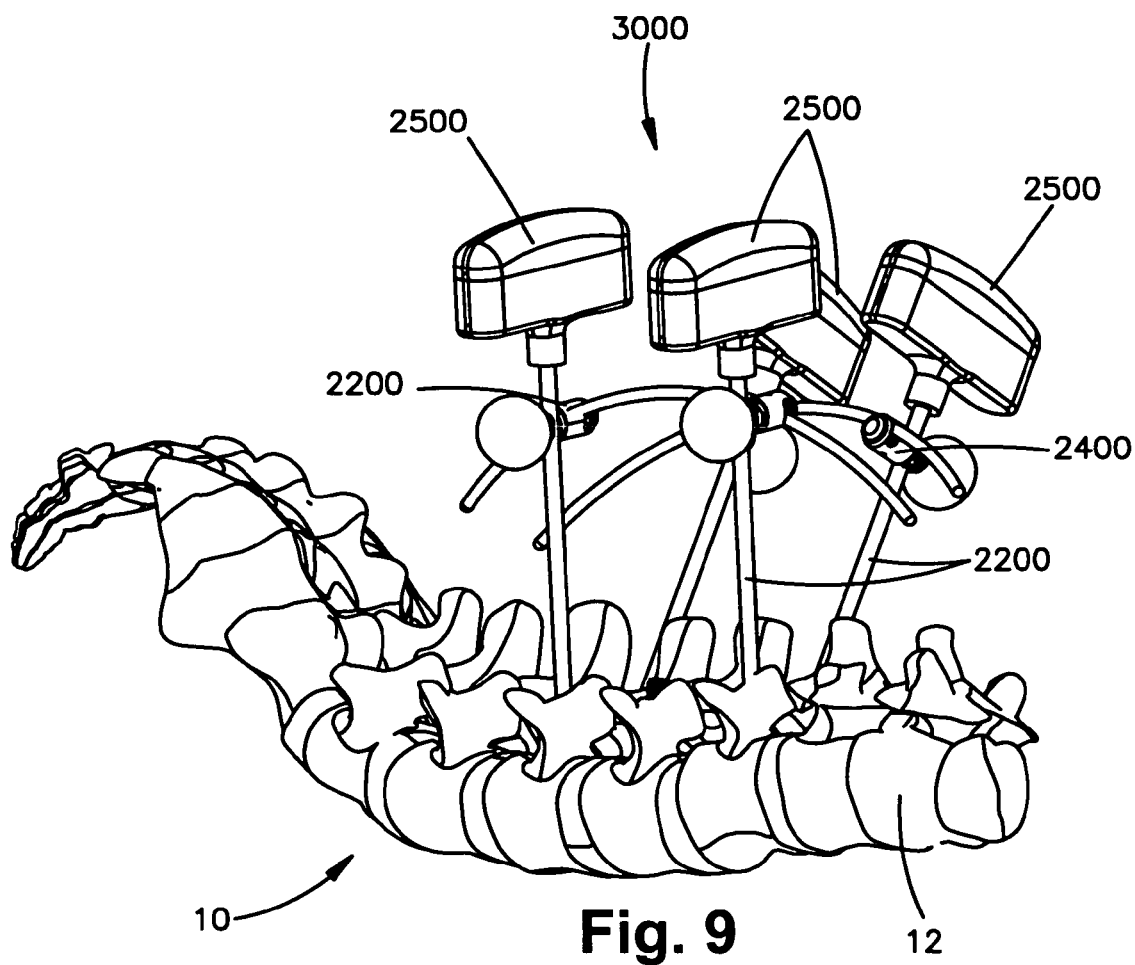
FIG. 9 is a perspective view photograph of an external fixator in use with a model spine.

FIG. 9 depicts an embodiment of device 3000 showing members 2200 inserted into vertebra 12 of a spine 10, and secured to one or more fixation members 2300, which may have an arcuate shape. Members 2200 may be secured to the fixation members 2300 using clamps 2400, which may be, for example, standard fixation clamps known in the art. Handles 2500 on each member 2200 may be used to insert and/or manipulate members 2200.

Figure 10:
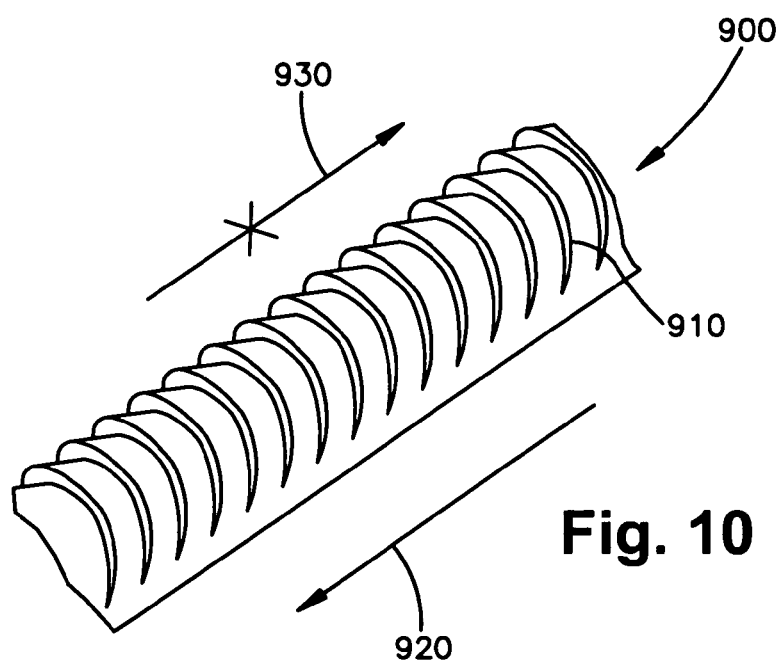
FIG. 10 is close-up perspective view of a fixation rod according to an embodiment of the present invention.

FIG. 10 shows a side view of a rod 900 that may be used as longitudinal member 2400, for example to secure members 2200 and/or cannula 2100 in a desired position. Rod 900 may include ridges or notches 910, which may be crenate, or scalloped, for example in order to allow movement of a clamp or other device (e.g., clamp 4000 of FIG. 11) in one direction 920 but not in an opposite direction 930.

Figure 11:
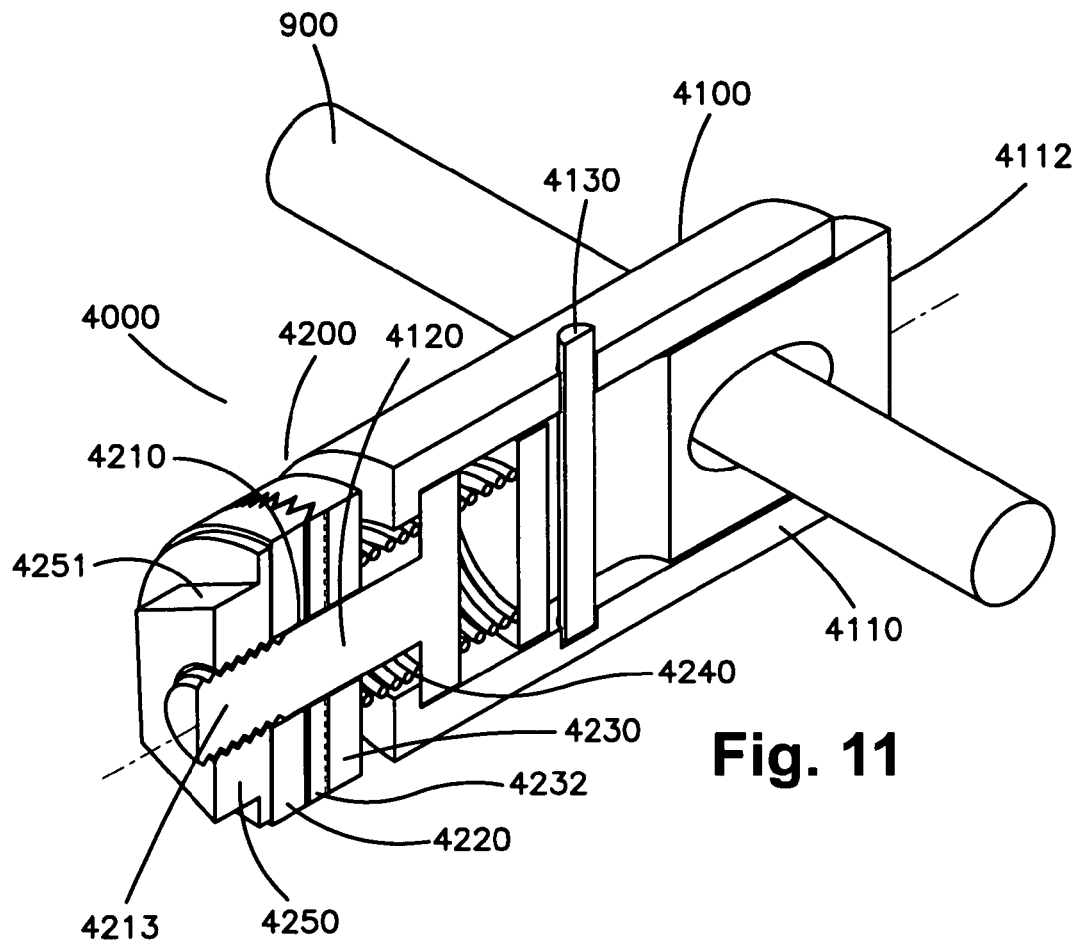
FIG. 11 is a side view of a clamp secured to a fixation rod according to an embodiment of the present invention.
Figure 12:
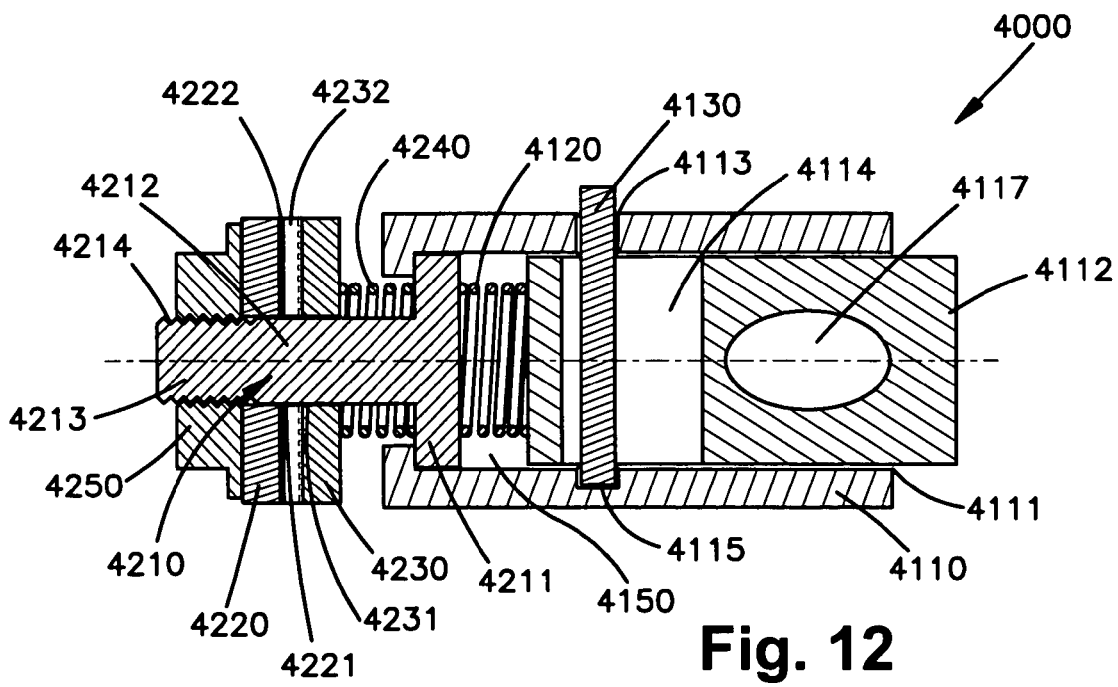
FIG. 12 is a side cross-sectional view of the clamp of FIG. 11.

FIGS. 11 and 12 show a side view of a selectively engageable clamp 4000, which may be used in conjunction with rod 900, for example instead of a clamp 2400. Clamp 4000 may comprise a first portion 4100 configured to selectively engage a rod 900, and a second portion 4200 coupled with portion 4100 and configured to adjustably engage a cannula or other elongated member that may be fixed to a vertebral body. Selectively engageable first portion 4100 may comprise, for example, a housing 4110 having an open end 4111 and an inner body 4112 which may be positioned partially within housing 4110 and extend from open end 4111. A biasing member 4120 may be disposed in a space 4150 within housing 4110, for example between inner body 4112 and a member 4211 of bolt 4210 of portion 4200. Biasing member 4120 may provide a biasing force that may tend to force inner body 4112 out through opening 4111.

One or more holes 4113 in housing 4110 may be dimensioned to pass a pin 4130, which may, for example pass through an elongated opening 4114 of inner member 4112, so that inner body may be movable with respect to housing 4110, but retained by pin 4130 within housing 4110. A socket 4115 or a hole or other feature in housing 4110 positioned opposite hole 4113 as shown in FIG. 12, may be configured to engage and secure pin 4113.

Housing 4110 may comprise a lateral opening (not shown) and inner body 4112 may comprise a lateral opening 4117 (as shown in FIG. 12). Openings 4116 and 4117 may be circular, elliptical, or any other desired shape. For example, as shown in FIG. 12, opening 4117 of inner body 4112 is substantially elliptical. Inner body 4112 may function as a button with respect to housing 4110. For example, pushing inner body 4112 into housing 4110, and against the force of biasing member, may align openings 4116 and 4117 such that rod 900 may move freely along its length. When button is released, biasing member may force inner body 4112 outward, which may change alignment of holes 4116 and 4117, for example such that notches 910 of rod 900 engage an edge of housing surrounding hole 4116 and prevent movement of clamp 4000 with respect to rod 900 in at least one direction. Using this mechanism, and because of crenate notches 910, clamp 4000 may slide over rod 900 in one direction, but not in the opposite direction without depressing the inner body 4112 (e.g., button) into housing 4110 to align openings 4116 and 4117.

Portion 4200 of clamp 4000 may be configured to engage and secure a member, e.g., elongated member 2200 or a cannula, a rod, a trocar, an introducer, a wire, a pin, or any other elongated member suitable for insertion into, or other attachment to, a vertebral body 12. Portion 4200 may comprise a bolt 4210 or screw coupled with housing 4110, one or more vice plates 4220, 4230 engaged with bolt 4210, a biasing member 4240 that may tend to keep plates 4220, 4230 closed, and a nut 4250 which may tend to oppose biasing member 4240 and to tighten vice plates 4220, 4230 around a member 2200 (not shown). The bolt 4210 may comprise a member 4211 located within housing 4110, attached to a shaft 4212. The end 4213 of shaft 4212 may be threaded 4214.

The vise plates 4220, 4230 may have an opening 4221, 4231, respectively, through which the bolt 4210 may be passed. In this way, the vise plates 4220, 4230 may be secured over bolt 4210, for example between nut 4250 and housing 4110. Each vise plate 4220, 4230 may also have a receiving portion 4222, 4232, respectively, for engaging and holding a member 2200 or other elongated member.

Biasing member 4240 (e.g., coil spring, wave washer, radial spring) may be positioned between the first vise plate 4230 and housing 4110. In this way, when the nut 4250 is connected to the base 4210 but not completely tightened thereto, a bone connection element may be clipped or snapped between the vise plates 4220, 4230, for example by inserting the bone connection element into the receiving portions. Such a construction may allow a bone connection element to be provisionally held between the vise plates 4220, 4230, for example, in front of nut 4250.

Moreover, the vise plates 4220, 4230 have features to facilitate proper alignment of the vise plates. For example, the second vise plate 4230 may have at least one protrusion (not shown) extending therefrom, and which may be received in at least one recess (not shown) in the first vise plate 4220. In this manner, the vise plates 4220, 4230 can both rotate together to orient the receiving portions 4222, 4232. One will appreciate that various other pins, protrusions, indentations, couplers or other alignment features may be used.

In order to tighten the nut 4250, nut 4250 may have a gripping portion 4251 (e.g., serrated or knurled portion) which may facilitate hand-tightening of the nut 4250. Alternatively or in addition, other features to facilitate engagement of a wrench or other tool may be provided on nut 4250. Those skilled in the art will appreciate that other clamps may also be used with the external fixation system shown and described.

Figure 13A:
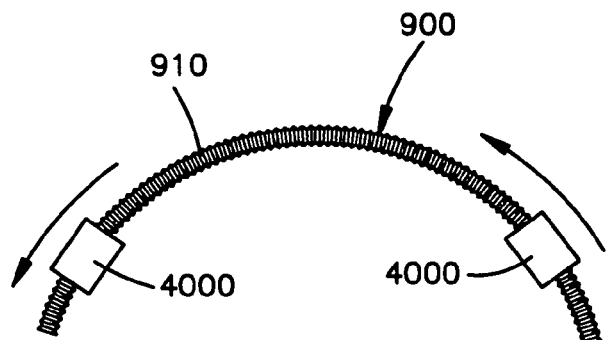
FIGS. 13A and 13B are side view schematic illustrations showing operation of the clamp and fixation rod of FIG. 11.
Figure 13B:
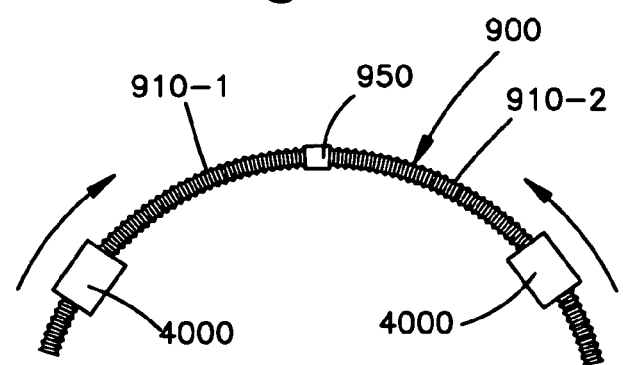

FIGS. 13A and 13B is a schematic diagram showing a rod 900 having notches 910 or other features which may engage one or more clamps 4000. Clamps 4000 may engage with notch features 910 and move along rod 900 in a particular direction, depending for example, upon the direction of the notch features 910.

Two rods 900 may be attached together via connector 950, such that the directions of the notches 910-1 and 910-2 are in opposite directions. Thus, the repositioning, i.e., moving of the clamps may occur in opposite directions as indicated by arrows 2710 and 2720 in FIG. 14.

Figure 15:
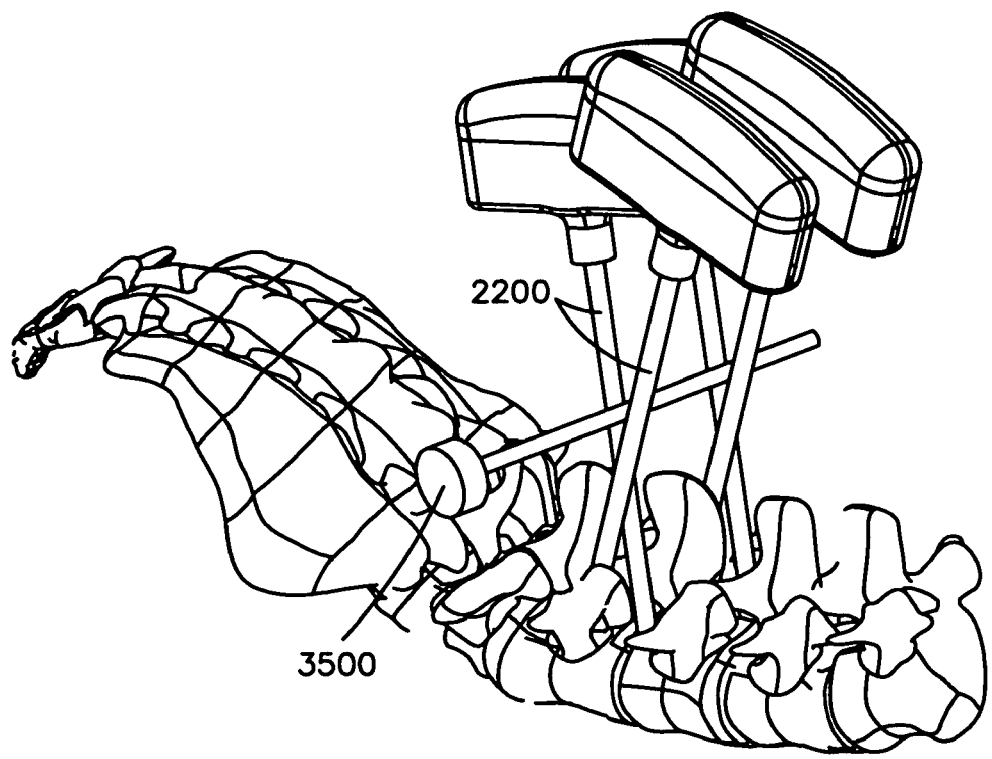
FIG. 15 is a perspective view of fixation device with elongated members crossing over each other.
Figure 16:
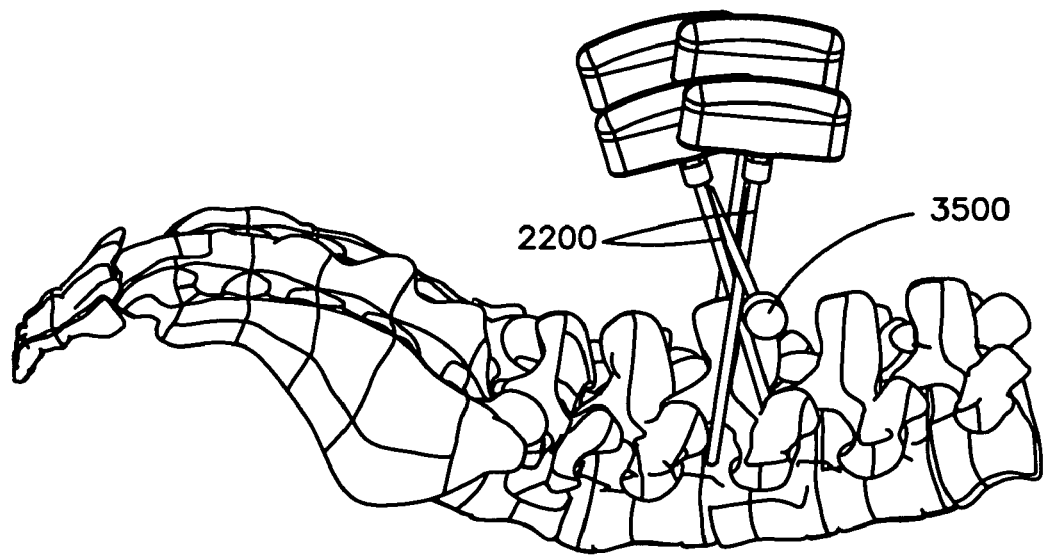
FIG. 16 is a perspective view of fixation device with elongated members crossing over each other from a different angle than FIG. 15.
Figure 17:
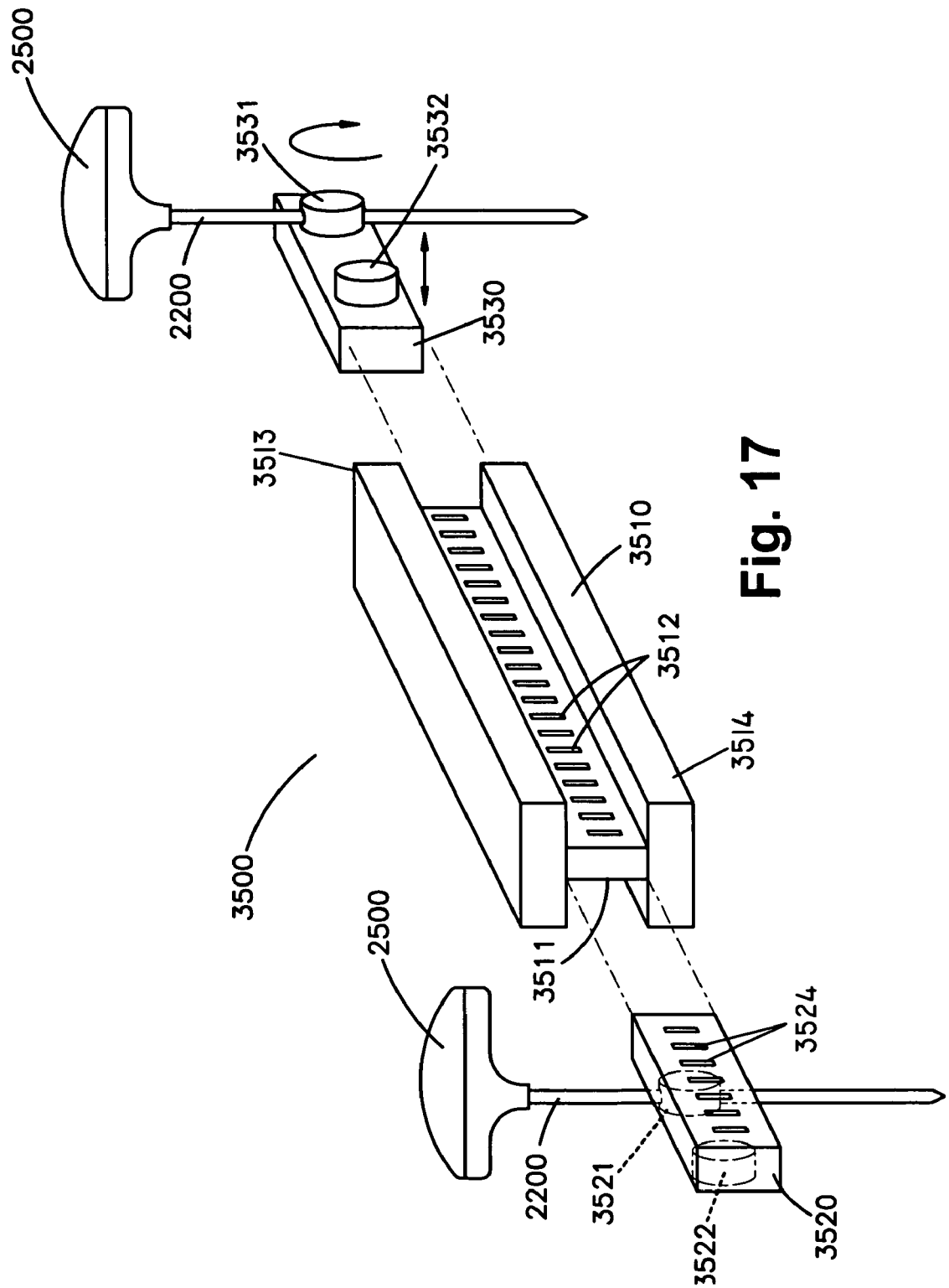
FIG. 17 depicts an adjustable gliding mechanism.
Figure 18:
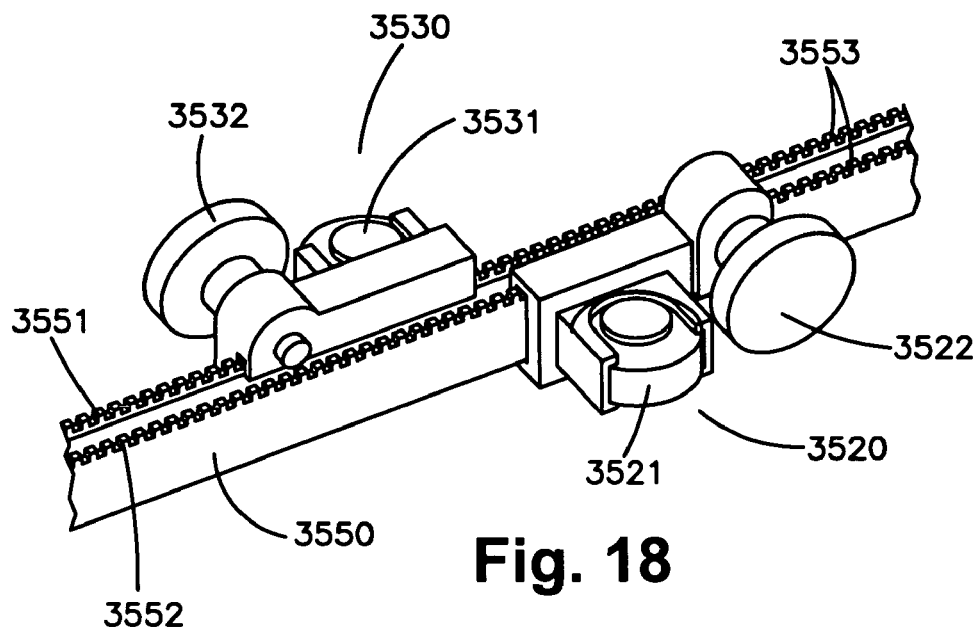
FIG. 18 depicts another embodiment of an adjustable gliding mechanism.

In order to further distract/move the spine using a fixation device 3000 as shown in FIGS. 5, 6, and 14 it may be necessary to have the elongated members 2200 crossing each other (FIGS. 15 and 16), for example using an adjustable gliding mechanism 3500 (FIGS. 17 and 18). FIGS. 15 and 16 depict the adjustable gliding mechanism 3500 connected to the elongated members 2200.

FIGS. 17 and 18 depict two embodiments of the adjustable gliding mechanism 3500 which are function similarly. The adjustable gliding mechanism 3500 depicted in FIG. 17 includes a slidable member 3510 which may have an "I-bar" configuration, where the vertical member 3511 has notches 3512 on both sides to allow position members 3520, 3530 to move along the length of the slidable member 3510. The position members 3520, 3530 fit between the horizontal members 3513, 3514 of the slidable member 3510 and mate with the vertical member 3511. Each position member 3520, 3530 may have protrusions, or other means, 3524 on a mating side 3523, 3533 which correspond to the notches 3512 on the slidable member 3510. The position members 3520, 3530 also may include a release button 3522, 3532 that when activated by, for example, depressing the button, the position members 3520, 3530 are able to move along the slidable member 3510. That is, for example, the protrusions 3524 disengage from the notches 3512 and the position members 3520, 3530 are able to slide between the horizontal members 3513, 3514 along the length of the slidable member 3510. The position members 3520, 3530 may be held between the horizontal members 3513, 3514 by, for example, a lip (not shown) extending from each horizontal member. Each position member 3520, 3530 may have attaching units 3521, 3531, allowing elongated members 2200 to be attached to the position members 3520, 3530. The attaching units 3521, 3531 may be rotated to adjust the angle of the elongated members 2200, for example, so that they may cross-over with respect to one another.

FIG. 18 depicts an alternative embodiment of a slidable member 3550 of the adjustable gliding mechanism 3500. In this embodiment, the slidable member 3550 has two tracks 3551, 3552 parallel to one another. Each track 3551, 3552 may have teeth 3553 or other means for allowing incremental movement of the position members 3520, 3530. The position members 3520, 3530, having attaching units 3521, 3531 and release buttons 3522, 3532, function similarly as in the previous embodiment.

Figure 19:
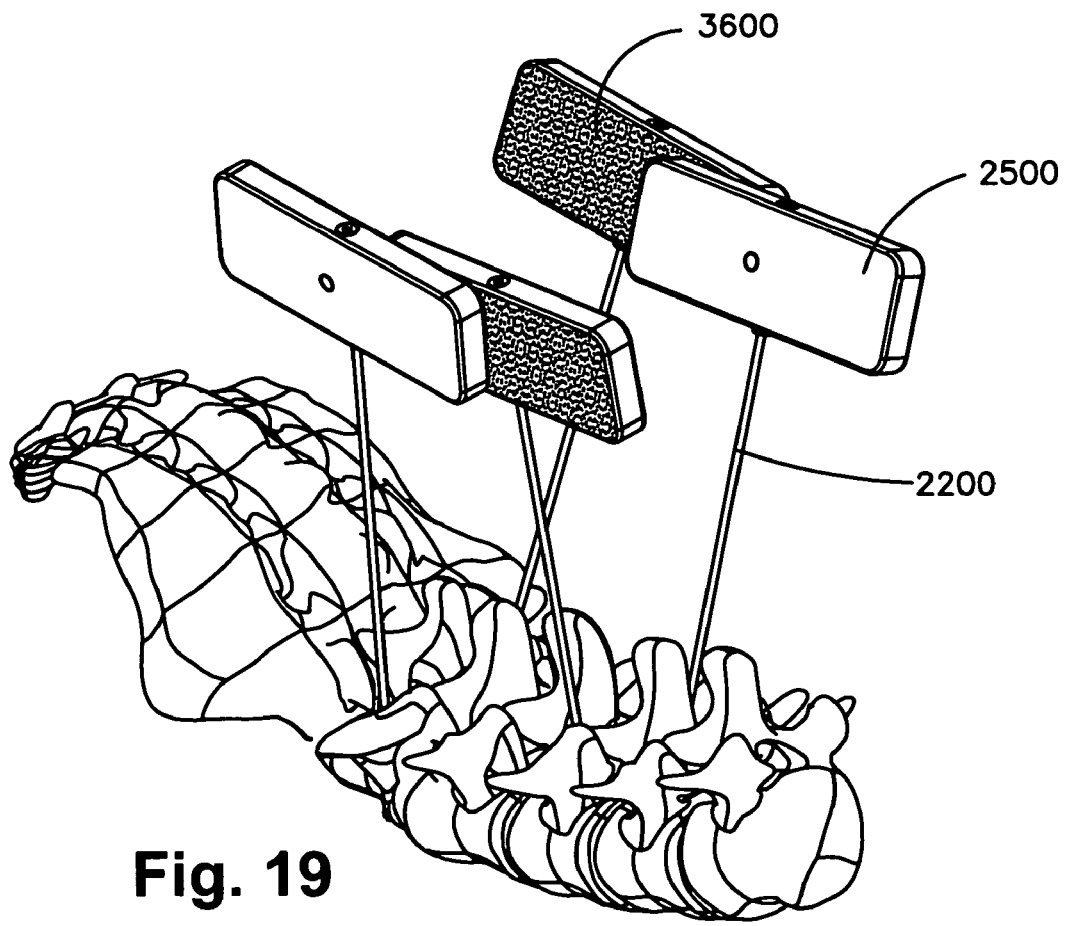
FIG. 19 depicts an alternative device for repositioning vertebrae.

FIG. 19 depicts an alternative device for repositioning vertebrae. In lieu of a fixation device 3000, as described previously, the elongated members 2200 extending out from the vertebrae may have Velcro fasteners 3600 attached to their proximal ends 2220. After manipulation of the elongated members 2200 to restore the lordosis, for example, by manually manipulating and controlling the elongated members 220, the positions of the elongated members 2200 with respect to each other may be secured by sticking together the elongated members 2200 which are equipped with Velcro fasteners 3600. The Velcro fasteners 3600 may be attached directly onto the handles 2500 of the elongated members 2200 or an additional cap (not shown) may be slipped over the handle 2500. Alternative methods for attaching the Velcro fasteners 3600 to the handles 2500 are envisioned.

Once the spinal segment is decompressed and repositioned, the fractured vertebral body can be surgically treated.

Disrupt Healed Fracture (Step 1300)

Before or after repositioning vertebrae 12a and/or 12c in the region of a fractured vertebral body 12b, it may be necessary that the anterior portion 22 of collapsed vertebral body 12b, and in particular the cortical shell 14, be re-fractured, dissociated or otherwise disrupted. Such a procedure may be particularly useful to prepare a vertebral body for repositioning of the vertebral endplates 20 and 30 and/or augmentation, for example in situations where the fractured bone has healed or partially healed over a period of time, e.g., six weeks or more. Various types of disruption devices may be used to fracture the damaged cortical bone 14, for example a chisel 800 as shown in FIG. 20, a laser 900, or another instrument.

FIG. 20 shows a disruption device or chisel-like device 5000 which may comprise an elongated member 5410 having a proximal tip 5420 which may be configured to break apart bone or other rigid structures. Elongated member 5410 may be approximately cylindrical although other shapes are contemplated. Tip 5420 may have a variety of shapes as described herein, for example tip 5420 may be tapered as shown in FIG. 20 to provide a knife-like tip for disrupting bone. Tip 5420 also may be at least partially blunted to help minimize damage to surrounding tissue. A handle 5430 may be attached to a distal end 5432 of elongated member 5410, e.g., opposite tip 5420.

As shown in FIG. 20, disruption device 5000 may be inserted into a vertebra, for example through a cannula 5440 inserted using a posterior approach, such that tip 5420 passes through central portion 50 of a vertebral body 12 and contacts the cortical bone 14 on the anterior side 22 of the vertebra 12. Cannula 5440 may or may not be similar to the cannulae described previously.

In some embodiments, cannula 5440 comprises a rigid member 5442 which may be threaded into a hole in pedicle 24, and an elongated member 5444, which may be cylindrical and dimensioned to extend out of the vertebra and surrounding soft tissue to provide minimally invasive access for device 5000 into vertebral body. Elongated member 5444 may be flexible and may be coupled, e.g., permanently coupled or releasably coupled, with rigid member 5442 at coupling 5446. Rigid member 5442 may be configured and dimensioned for insertion into a vertebra, e.g., into a central portion of a vertebral body 12 from a posterior approach through a pedicle 24. In some embodiments, a hole may be formed through the outer cortical bone of vertebra 12, e.g., through pedicle 24, e.g. by a drill, trocar, or other instrument. Coupling 5446, where rigid member 5442 couples with member 5444 may be at a location inside or outside of pedicle 24 of vertebra 12. In other embodiments, another type of cannula, trocar, or other introducer may be used to provide access for disruption device 5000 to a vertebra 12 or other bone.

The diameter of member 5410 of device 5000 may be, for example, between about 2 and 10 mm. Member 5410 of device may have any desired length, for example between about 20 and 70 cm. Handle 5430 may also have any desired length, for example between about 4 cm and 20 cm. Device 5000 may comprise stainless steel, a metal, a metal alloy, a polymer, a composite, a ceramic or a combination thereof.

Elongated member 5410 may include a sleeve 5422 or other device or member disposed around and/or attached to member 5410, and sleeve 5422 may be dimensioned to limit the amount of axial movement of member 5410 into vertebral body 12, for example by contacting coupler 5446, as will be described in more detail later.

As shown in FIG. 21, one, two or more disruption devices, e.g., 5000-1 and 5000-2, may be inserted into vertebral body 12, for example through one or more cannulae 5440 as described with respect to FIG. 20. Cannulae 5440 may have a rigid member 5442, and rigid member 5442 may include threads 5443 for securing to vertebra, e.g., through pedicles 24 as shown. In some embodiments, rigid member 5442 may include a nut feature 5447 having substantially flat surfaces or other surfaces that may be configured to engage with a wrench or other tool for screwing and/or otherwise fitting rigid member 5442 into bone 12. Coupling 5446 may provide a releasable coupling, e.g., between member 5444 and rigid member 5442.

Device 5000 may have different configurations, for example as shown by device 5000-1 and 5000-2 of FIG. 21. Device 5000-1 is shown with elongated member 5410-1 having a relatively uniform diameter. In such embodiments, member 5410-1 may move freely in an axial direction through cannula, for example toward cortical bone 14 at anterior end 22 of vertebral body. In other embodiments, such as, for example, device 5000-2, member 5410-2 may include a stop 5512 or other feature that limits axial movement of member 5410-2 within cannula 5440. For example, as member 5410-2 moves proximally, toward the anterior aspect 22 of vertebra 12, stop 5512 may contact edge 5510 of coupler 5446, thereby inhibiting or preventing further movement of member 5410-2 into vertebral body. Stop 5512 may be provided, for example, by a sleeve 5422 surrounding a portion of member 5410-2, and may be dimensioned and/or adjustable to provide a desired range of axial movement of member 5410-2 into vertebral body 12.

FIGS. 22A and 22B show close up illustrations of tips 5420, e.g. tip 5420-1 and 5420-1. Tip 5420 may have any desired configuration, for example to cut through, break up, or otherwise disrupt cortical bone 14 of vertebra 12, e.g., after bone 14 has healed in a collapsed state after an injury, for example, as a result of a vertebral compression fracture. Tip 5420 may be tapered in one or more dimensions, for example tapered to provide a knife or chisel-like tip as shown by tip 5420-1. In other embodiments, tip 5420 may have another configuration, for example, a paddle-like configuration as shown by tip 5420-2, wherein tip may have a width that is greater than the diameter of member 5410-2. Additional details regarding tip 5420 and/or member 5410 configurations are described elsewhere herein, for example with respect to FIGS. 28-30.

FIG. 23 shows a perspective view of a spine with cannulae 5440 or other introducers being inserted into the posterior aspect of vertebrae 12, for example using a tool 5700 having a handle 5710 to insert cannula 5440 through pedicles 24. Various types of cannulae which may be suitable for providing passage of devices 5400 into vertebrae 12.

Figure 24:
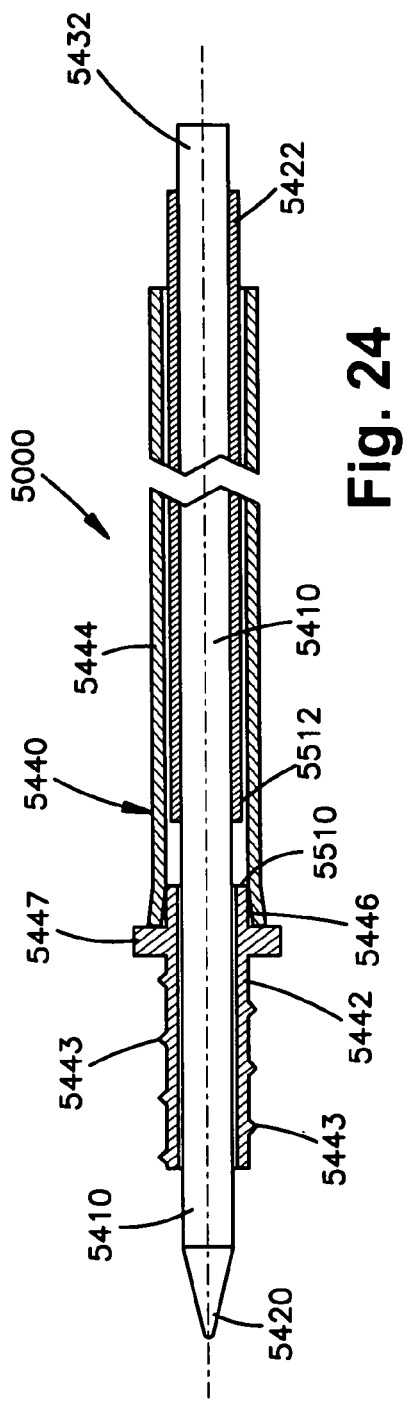
FIG. 24 is a schematic cross-sectional side view of a disruption apparatus and a cannula according to an embodiment of the present invention.

FIG. 24 shows a cross-sectional view of a disruption device 5000, which may or may not be used in conjunction with cannula 5440 as described above. Disruption device 5000 may include an elongated member 5410 dimensioned to pass through cannula 5440, e.g. through rigid member 5442 and member 5444. A sleeve 5422 or other member may be disposed around member 5410 and may be dimensioned and/or positioned such that an end 5512 of sleeve 5422 may contact proximal end 5510 of coupler 5446 of rigid member 5442 as device 5000 is advanced axially into a vertebral body or other bone. Sleeve 5422 may be attached to and/or may be slideable or adjustable over member 5410, for example to provide a desired range of motion of device 5000 into vertebrae.

Proximal end 5432 of member 5410 may be configured and dimensioned as desired to engage with handle 5430, as described in more detail, for example, with respect to FIG. 26.

Figure 25:
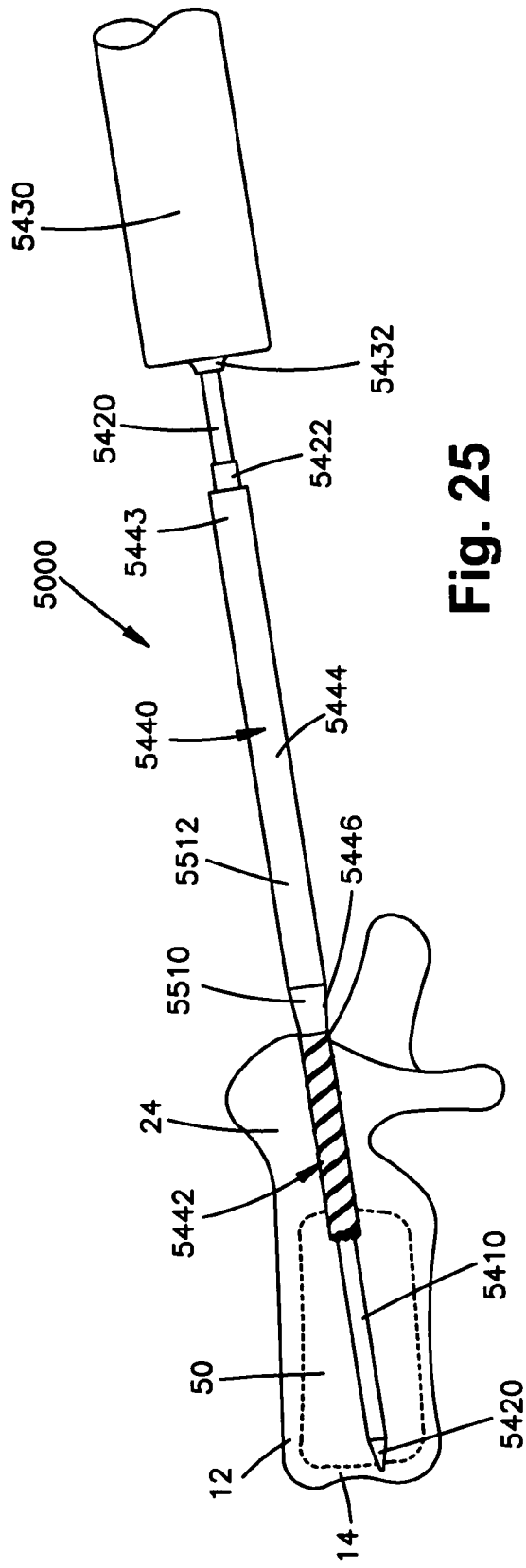
FIG. 25 is a side view of a disruption device inserted into a vertebra according to an embodiment of the present invention.

FIG. 25 is another side view of a disruption device 5000, in use in a vertebra 12. Elongated member 5410, tip 5420 and cannulae 5440 may be as described above. In this example, sleeve 5422 may be dimensioned to fit inside of cannula 5410. Sleeve 5422 may include projections 5433 that may extend outward and run longitudinally along the long axis of the member 5410. Such projections 5443 may be useful for providing a limit stop for device 5000, e.g., by contacting a distal end of the rigid portion 5442 of the implant 5440 as device 5410 is pushed through cannula 5440 and space 50 of vertebra 12, toward bone 14.

FIG. 26 is a top view of a disruption device 5000 having a tip 5420 that is inserted through a cannula 5440 and into a vertebra 12 to contact and disrupt bone 14. Device 5000 may include a sleeve 5422 or other mechanism to limit or control the depth of penetration (shown by "T") of tip 5420 into the cortical bone 14 on anterior portion of the vertebra 12. Distal end 5432 of elongated member 5410 may secure or otherwise couple with handle 5430, for example within a socket 5434. In some embodiments, sleeve 5422 may contact end 5432 at socket 5434. Socket 5434 and end 5432 may be configured and dimensioned to releasably, adjustably, or fixedly couple to one another. For example, socket 5434 may be threaded and end 5432 may have corresponding threads, such that, for example the depth of penetration "T" of device may be adjusted by adjusting the amount that end 5432 is disposed within socket 5434 of handle 5430.

FIG. 27 is a side view of a disruption device 5000 in use in a vertebral body 12 to dissociate bone that may have healed in a collapsed or fractured position. Device 5000 includes sleeve 5422 as described above, and the sleeve may function to limit movement of the tip 5410 through bone 14. Such limits may be desirable, for example, in situations where tissues surrounding the area to be dissociated may be fragile or sensitive. Arrow 1 shows an area of bone 14 that may be damaged and that may be disrupted and potentially later repaired using methods described herein.

As shown in FIG. 28, the end of device 5000 may be inserted into a vertebra 12, e.g., using a hammer 2 to advance device 5000 into an anterior portion of a vertebra 12, for example using a tip 5420 configured with a sharp, semi-sharp, or blunt tip for contacting bone. That is, device 5000 may be impacted against bone, for example, using hammer 2. In other embodiments, a vibrator or other device is attached, for example, to handle 5430 and/or elongated member 5410, and used to move elongated members 5410, for example, longitudinally, transversely and/or in another direction into vertebra 12 and toward damaged bone 14.

FIG. 29 shows a close-up side view of a vertebra 12 and device 5000 which has elongated member 5410 and tip 5420 and shows the motions enabled by device 5000, such as transverse motion 3 and longitudinal motion 4.

Figure 30A:
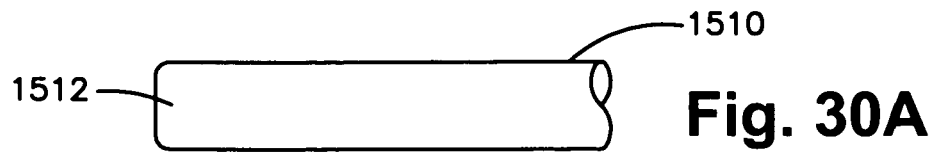
FIG. 30 is a top view schematic illustration of disruption device tips according to various embodiments of the present invention.
Figure 30B:
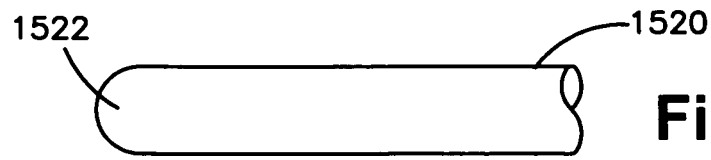
Figure 30C:
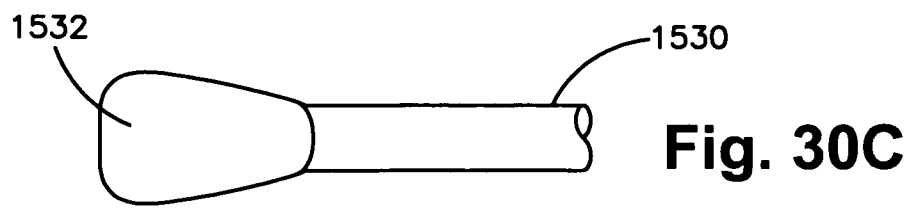
Figure 31A:
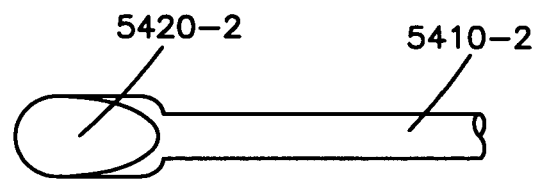
FIGS. 31A and 31B are top views of different device tips according to an embodiment the present invention.
Figure 31B:
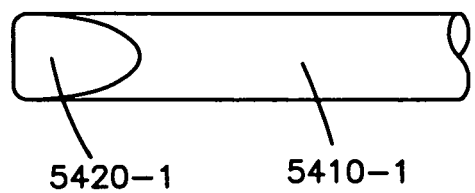
Figure 32A:
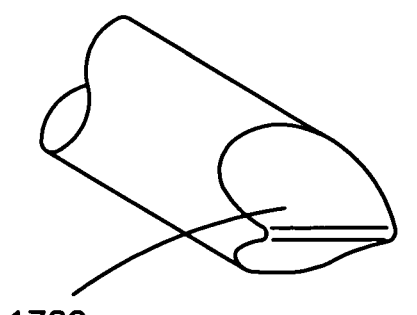
FIGS. 32A and 32B are perspective end view of two device tips according to an embodiment of the present invention.
Figure 32B:
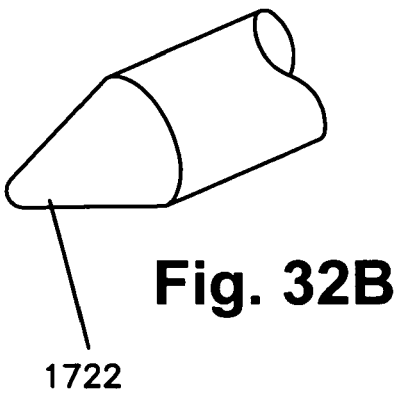

FIG. 30 shows a schematic illustration of examples of various tips 1512, 1522, 1532 that may be used to disrupt bone. FIG. 31 shows a top close-up view of member 5420-2 and tip 5420-2. FIG. 31 shows a top view of device 5410-2 in use in a vertebral body. FIGS. 32A and 32B are a close up of different types of tips 1720 and 1722.

As shown in FIG. 33, a laser 9000 or other tool for cutting or fracturing bone may be used instead of or in addition to a chisel or disruption device 5000 to break apart or otherwise disrupt the damaged cortical bone 14 of vertebral body 12b (FIG. 34). The laser 9000 may be dimensioned to pass through cannula 2100 and into the internal portion 50 of vertebra 12b.

FIG. 35 shows a schematic view of vertebral body 12b with cortical bone 14 re-fractured, for example using disruption device 5000 or laser 9000. The disruption device 5000 or laser 9000 has been removed from cannula 2100, for example in preparation for repositioning of endplates 20 and 30 to restore of the height of vertebral body 12b.

Restore Vertebral Body Height (Step 1400)

After re-fracturing or otherwise disrupting the cortical bone 14 of vertebral body 12b in step 1300 of FIG. 4, the height of vertebral body 12b, or distance between endplates 20 and 30, may be increased toward a normal height (e.g., a height of the vertebral body 12b prior to injury).

Figure 35A:
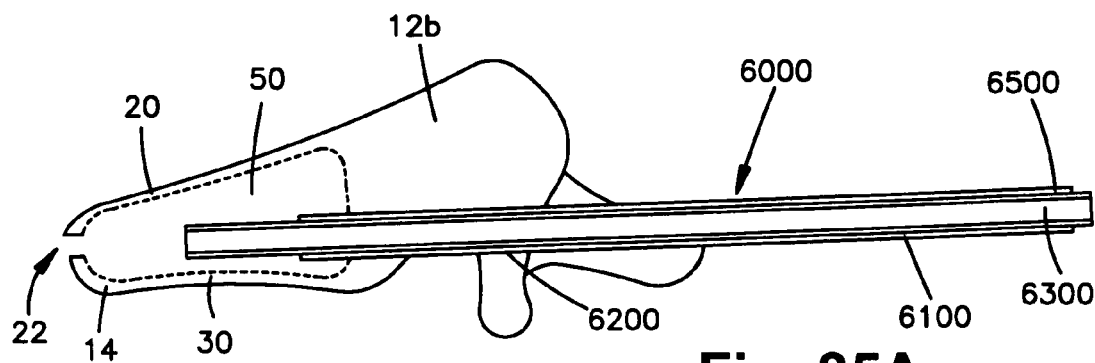
FIGS. 35A-D are schematic side view illustrations of a method of restoring the height of a fractured vertebral body.

An example of a method of restoring the height a vertebral body is shown in more detail in FIGS. 35A-D. For example, FIG. 35A shows a partially flexible cannula 6000 inserted into vertebral body 12b. Cannula 6000, being the same as or similar to cannula 100 described later, may comprise, for example, a proximal member 6100 and a distal member 6200. A rigid cannula, needle, trocar or other introducer 6500 may be used to facilitate placement of cannula 6000. For example, introducer 6500, which may be dimensioned to fit within lumen 6300 of cannula 6000, may first be inserted into a vertebral body through a pedicle as known by one of ordinary skill in the art. Cannula 6000 may then be slid over introducer 6500 and into position, such that distal member 6200 passes through pedicle 24 and into the central portion 50 of vertebral body 12b.

Proximal member 6100 may attach or couple to distal member 6200 and extend posteriorly from the spine through the soft tissue of the patient such as, for example, skin and muscle. Proximal member 6100 may be flexible or semiflexible to allow insertion of bent instruments or tools, and to help minimize damage to the pedicles 24 and surrounding soft tissue.

Figure 35B:
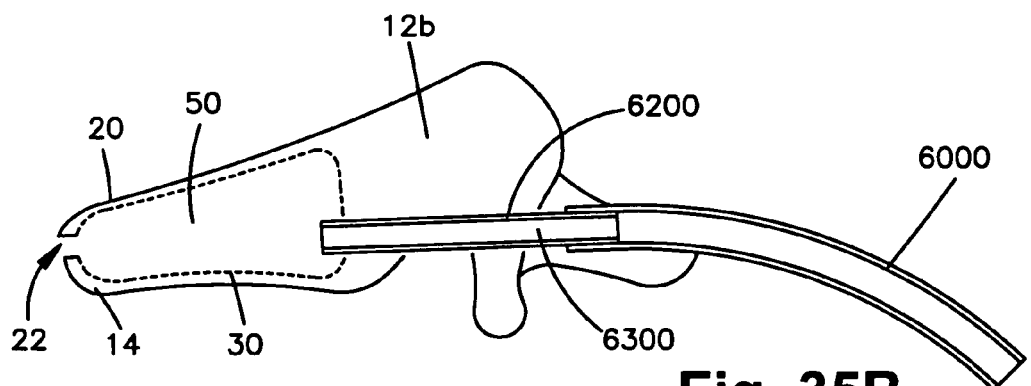

After insertion of cannula 6000, introducer 6500 may be removed, as shown in step FIG. 35B, e.g., to open lumen 6300 of cannula 6000 to provide a passage for insertion of a bent rod 6700 or another instrument, implant or filler into central portion 50 of vertebral body.

Figure 35C:
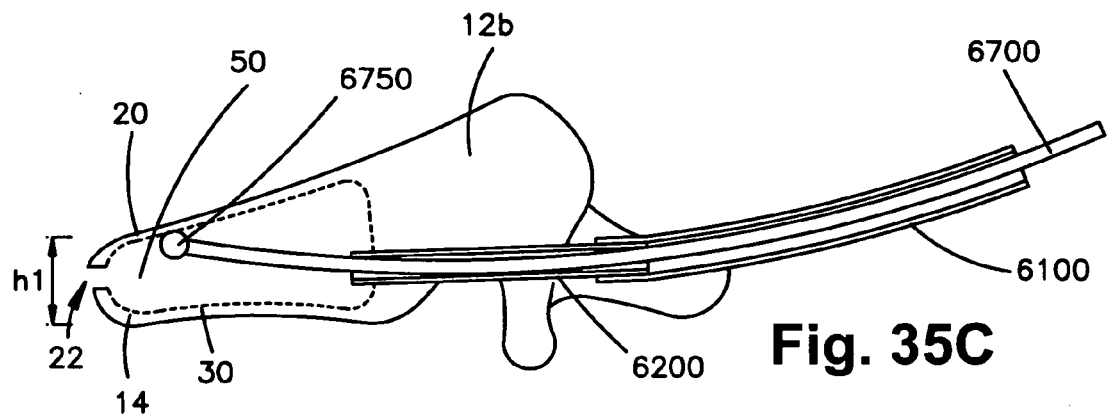
Figure 35D:
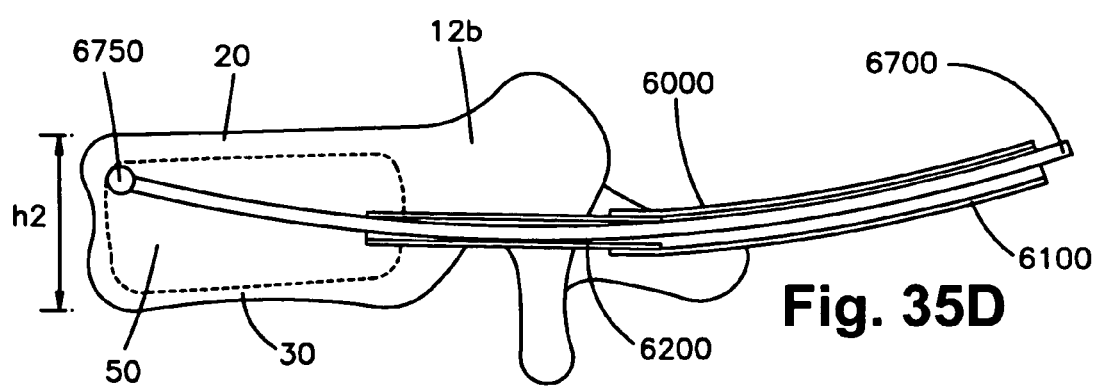

As shown in FIG. 35C, an instrument for repositioning the collapsed endplates of the damaged vertebral body may then be inserted through cannula 6000. For example, rod 6700 which may be bent and have a head 6750, can be inserted through lumen 6300 and can be used to push against upper endplate 20. Rod 1130 may be advanced into central portion 50 of vertebral body 12b as shown in FIG. 35C, and the bent rod 6700 may push apart the endplates 20 and 30 to restore the height of the vertebra 12b, for example from height h1 in FIG. 35C to height h2 in FIG. 35D. Rod 6700 may be configured different than illustrated in the FIGS. 35C and 35D and may comprise more than one piece or element and may comprise articulating pieces.

Figure 36:
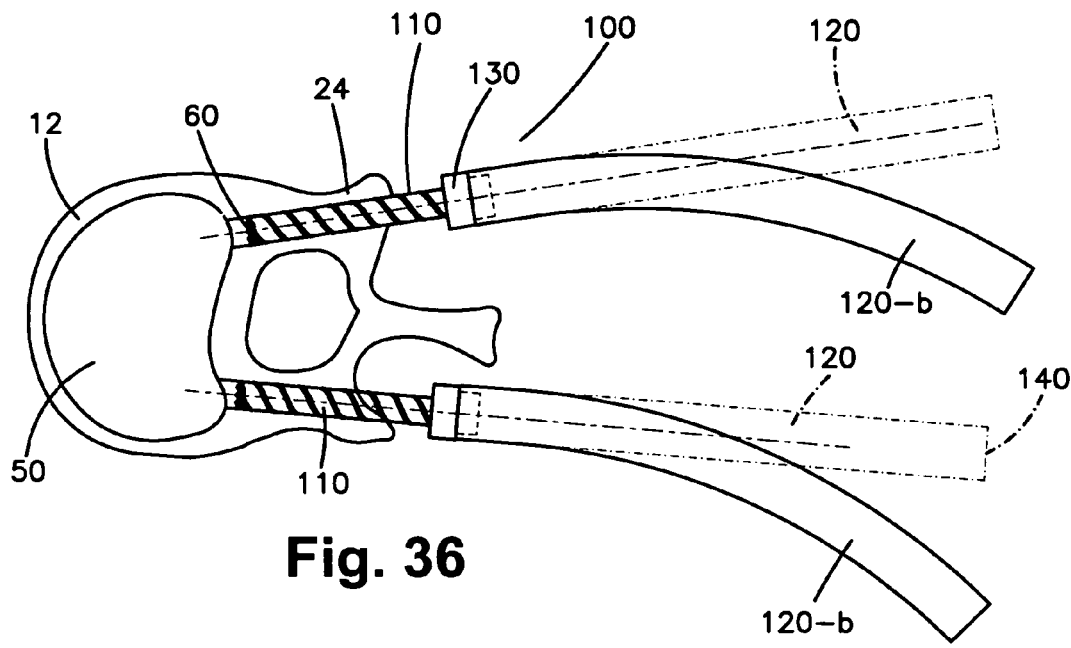
FIG. 36 is a top view of cannulae inserted into a vertebra according to an embodiment of the present invention.

In greater detail, one embodiment of a device for augmenting a vertebrae provides a cannula. FIG. 36 depicts a partially flexible cannula 100 which may comprise a rigid member 110 and a flexible member 120. Flexible member 120 may be coupled, e.g., permanently coupled or releasably coupled, with rigid member 110 at coupling/joint 130. Rigid member 110 may be configured and dimensioned for insertion into a vertebra, e.g., into a central portion 50 of a vertebral body 12 from a posterior approach through a pedicle 24. In some embodiments, a hole 60 may be formed through the outer cortical bone of vertebra 12, e.g., thorough pedicle 24, e.g. by a drill, trocar, or other instrument. Joint 130 where rigid member 110 couples with flexible member 120 may be at a location inside or outside of pedicle 24 of vertebra 12.

Cannula 100 may have a lumen 140 (e.g., see lumen 140 of FIGS. 38 and 42), which may form a passage though the rigid member 110 and the flexible member 120. Lumen 140 may be used to insert implants, instruments, tools, bone filler or other materials into central portion 50 of vertebra. The relative flexibility of flexible member 120, e.g., as illustrated by bent flexible members 120-b, may help minimize or prevent damage to the pedicle and/or the surrounding tissue during insertion or manipulation of various implants, instruments, tools, bone filler or other materials. The flexible member is generally located in and provides a passageway through soft tissue of the patient such as, for example, skin and muscle.

As shown in FIG. 36, one, two or more cannulae 100 may be inserted or implanted into a vertebral body 12. Where two cannulae are used, both cannulae 100 may be used to introduce instruments, implants and/or bone filler into the interior 50 of vertebra 12. The outer diameter of cannula 100 may be, for example, between about 3 and 12 mm, and the inner diameter may be between about 2 and 10 mm. Cannula 100 may have any desired length, for example between about 10 and 30 cm. Rigid member 110 of cannula 100 may have a length between about 20 and 70 mm, and may or may not correspond approximately to the length of pedicle 24. Cannula 100 may comprise any of stainless steel, a metal, a metal alloy, a polymer, a composite, a ceramic or a combination thereof.

Figure 37:
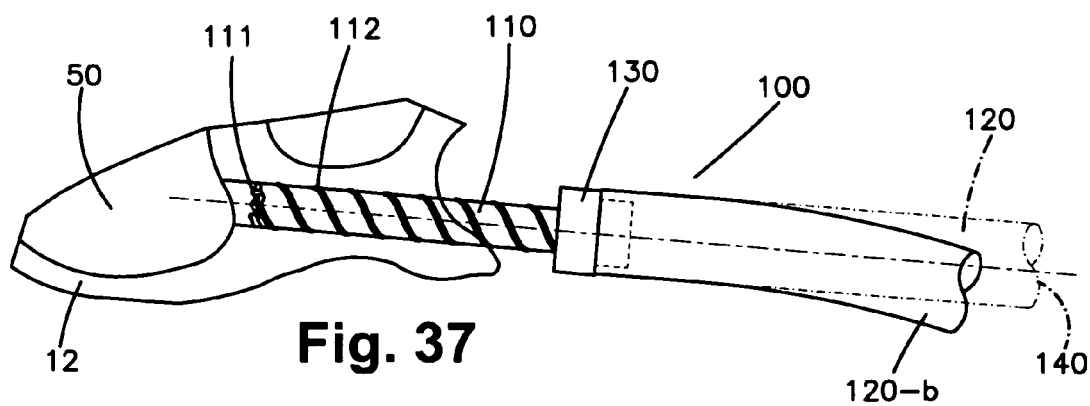
FIG. 37 is a close-up top view of a cannula of FIG. 36.

FIG. 37 provides a close-up top view of one of the cannulae 100 of FIG. 36, inserted through a pedicle 24 of vertebra 12. Specifically, rigid member 110 is shown inserted through pedicle 24 of vertebra 12. Rigid member 110 may be coupled with flexible member 120 at a coupling 130 just outside of posterior aspect of vertebra 12. Rigid member 110 may include threads 112 or ridges or other features that may facilitate insertion of rigid member 110, e.g., through vertebra 12. Rigid member 110 may further include a sharpened, serrated and/or toothed end (proximal end) 111 that may or may not work in conjunction with threads 112 to facilitate boring through a bone.

Figure 38:
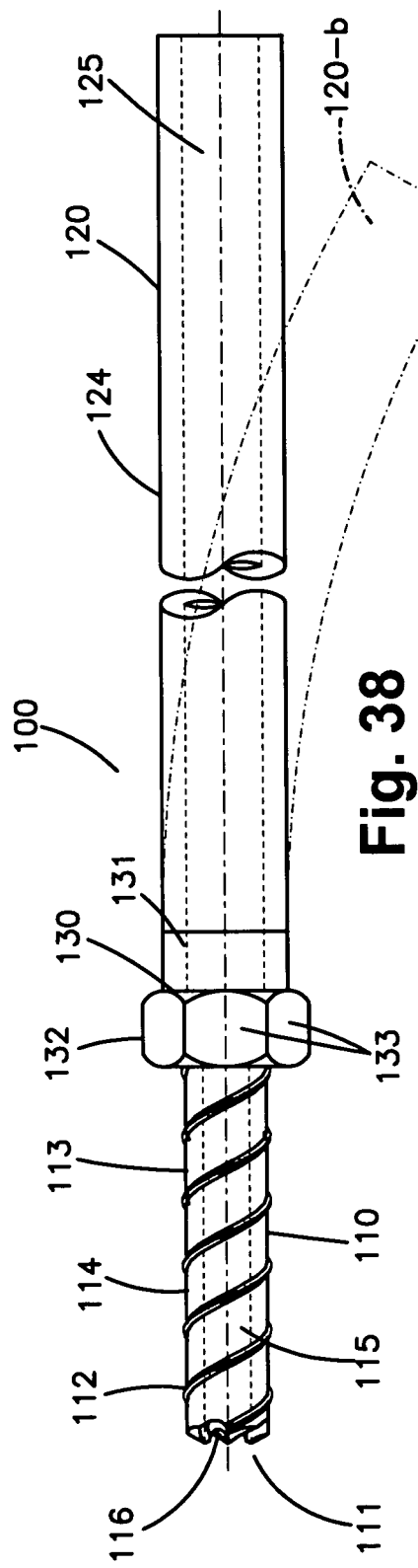
FIG. 38 is a schematic cross-sectional side view of a cannula according to an embodiment of the present invention.
Figure 39:
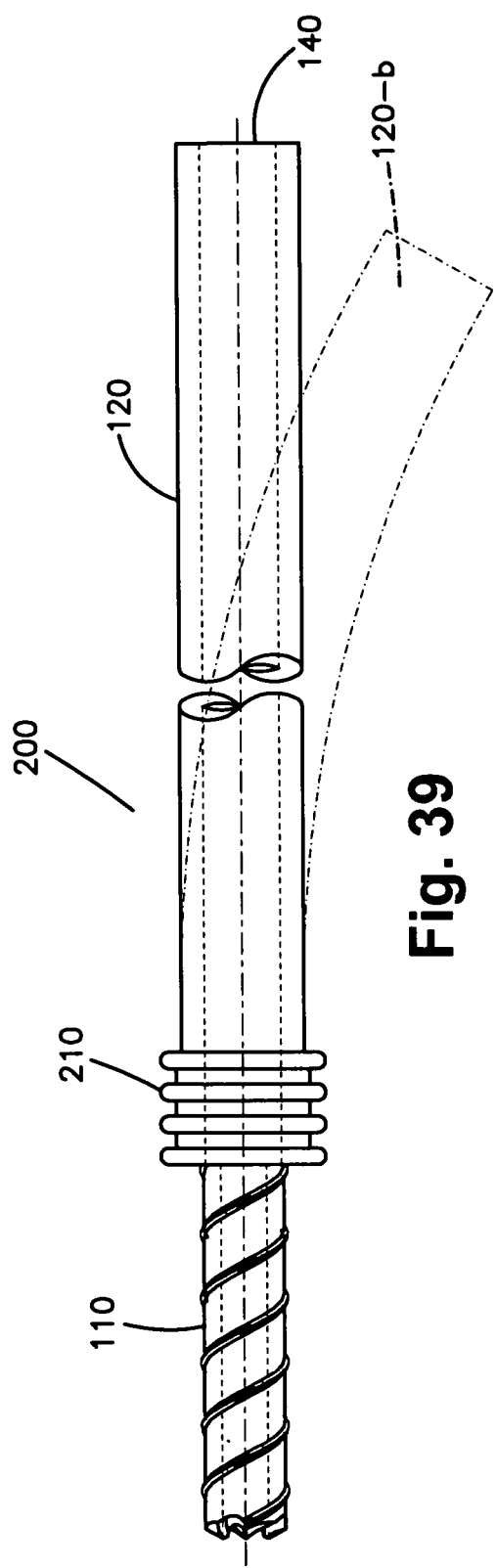
FIG. 39 is a cross-sectional side view of a cannula according to another embodiment of the present invention.

FIGS. 38 and 39 show additional details of cannulae 100. In some embodiments, rigid member 110 may have a shaft portion 113 having a length that is approximately equal to the width of pedicle 24, such that rigid member 110 may be completely implanted within pedicle 24, e.g., with only a small portion of rigid member extending posteriorly from the pedicle. As shown in the cross sectional diagram of FIG. 38, rigid member 110 and flexible member 120 each may comprise a substantially cylindrical wall 114 and 124, having an inner and outer diameter and defining a lumen 115 and 125, respectively. Lumen 115 and 125, may be joined, for example, at coupling 130, forming a lumen 130 through entire cannula 100.

Rigid member 110 may comprise a shaft or tube 113, which may or may not include threads 112. A proximal end 111 may be configured with teeth 116 or other cutting features that extend from the end of tube 113. Coupling 130 of cannula 100 may releasably or permanently couple rigid member 110 with flexible member 120. For example, as shown in FIG. 38, coupling 130 may include a slip fitting 131 that fits within lumen 125 of flexible member 120 and secures flexible member 120 with rigid member 110. A stop 132 on coupling 130 may provide a limit and/or seal for the coupling of flexible member 120 and rigid member 110. Stop 132 may include substantially flat surfaces 133 or other features that may be configured to engage with a tool (not shown), e.g., a wrench or other device for screwing and/or otherwise fitting rigid member 110 into a bone 12. Coupling 130 may provide a releasable coupling, between flexible member and/or rigid member.

Referring to FIG. 39, another embodiment of cannula 100 may comprise a rigid member 110 and a member 120. However, instead of being joined by a coupling 130 that allows member 120 to be disconnected from rigid member 110, rigid member 110 and member 120, may be formed as one-piece cannula 200. In such an embodiment, a coupling or joint 210 may include ridges 215 or other features that provide for flexibility or controlled bending of the cannula. More specifically, member 120 may be rigid similar to rigid member 110 but with a flexible joint 210 between rigid member 110 and 120. Member 120 may also be relatively flexible compared to rigid member 110 as provided in other embodiments.

Figure 40:
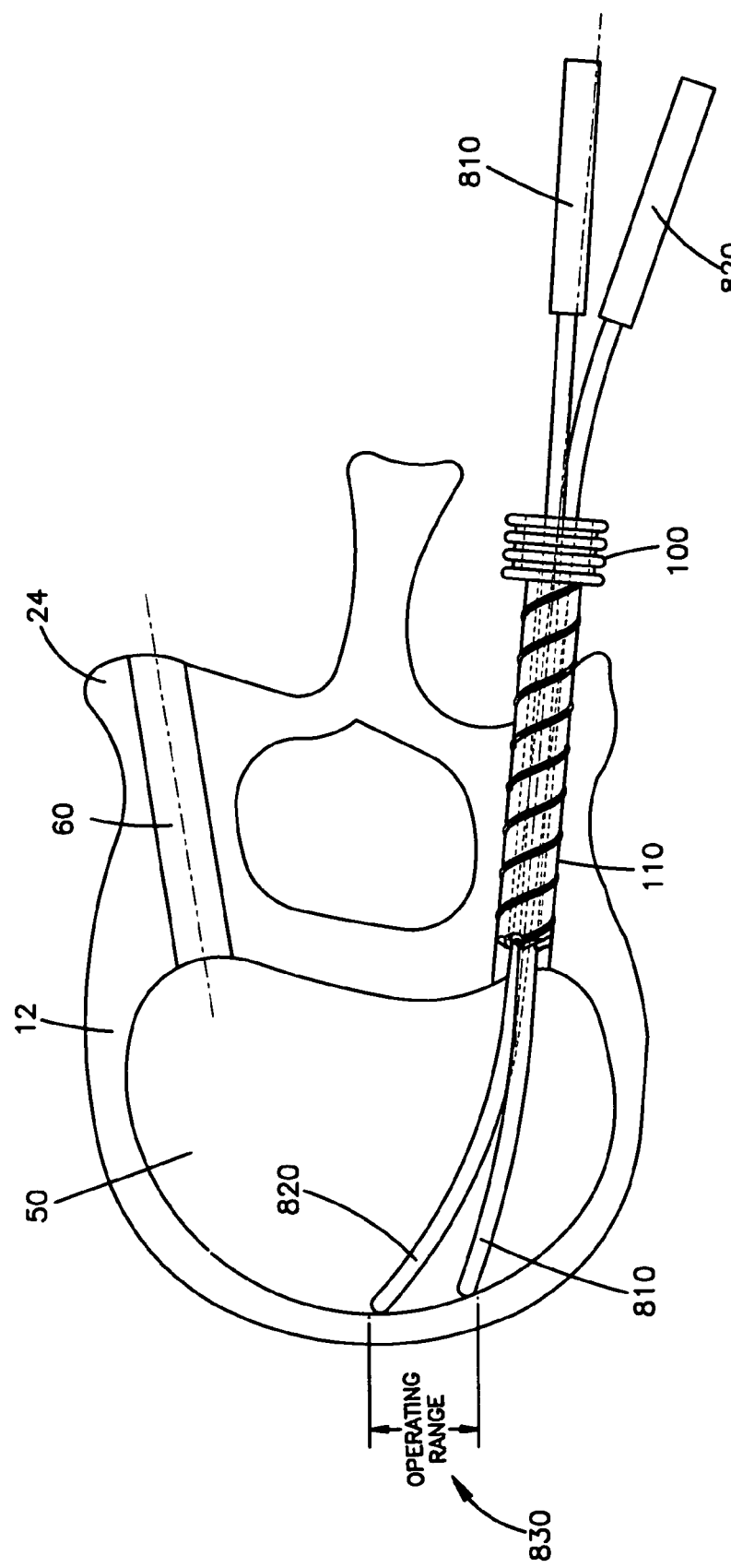
FIG. 40 is a top view illustration of a rigid member of a cannula according to an embodiment of the present invention.

FIG. 40 shows a rigid member 110 portion of cannula 100 inserted through an access hole, e.g., such as hole 60 in pedicle 24. The length of the rigid member 110 may generally correspond to the length of the pedicle 24 through which rigid member 110 is to be inserted. One or more instruments 810, 820 may be inserted into the interior portion 50 of vertebral body 12 through cannula 100. The instruments may be substantially straight as instrument 810, or curved as instrument 820. The flexible portion 120 of the cannula 100 (not shown in FIG. 40 for convenience of viewing instruments 810 and 820) allows for the insertion of bent or curved implants or instruments through cannula 100 and pedicles 24 into interior portion 50 of vertebral body 12. The operating range 830 of the bent implants or instruments 820 inserted through cannula 100 may be greater than straight implants or instruments 810.

FIGS. 41A and 41B illustrate an example of the use of a curved instrument 300 and 302 in conjunction with a rigid member 310 and 312, respectively. Rigid members 310 and 312 may be similar to rigid member 110 described above, and are separately identified here to illustrate a relationship between the length of a rigid member and the curvature of an instrument or rod that may be inserted through the rigid member. Rigid members 310 and 312 may be coupled with a flexible member 120 as described above, but such flexible members 120 are not shown for clarity of illustration. Rigid member 312 of FIG. 41B is substantially shorter than rigid member 310 of FIG. 41A. As illustrated, rigid member 312 can accept an instrument 302 having a greater curvature than can be accepted by longer rigid member 310. Thus, the amount of curvature of an instrument or implant that can be used with cannula 100 may depend, at least in part, on the length of rigid member 310, 312 (and 110), the diameter of the rigid member and the diameter of the instrument or implant shaft.

Turning now to FIGS. 42A and 42B, a bent rod 500 may be configured with a desired diameter and curvature to fit through a partially flexible cannula 100, and may be used for example to restore vertebral height in a collapsed vertebra 12. As rod 500 is inserted within cannula 100, flexible member 120 may curve with rod 500, and rigid portion 110 functions to confine and limit translations of rod 500 within vertebra 12. In some embodiments, a proximal end of rod may include a bulb or ball 510 that may enter central portion 50 of vertebral body 12 and engage an upper endplate 20 of vertebral body 12. The bulb 510 may serve to blunt the end of the rod 500 and to disperse pressure over a larger area. As rod 500 is advanced, as shown in FIG. 42B, end 510 of rod 500 pushes against endplate 20 and may increase the height of the vertebral body between upper endplate 20 and lower endplate 30. The end of rod 500, with or without bulb 510 may also compact cancellous bone in the vertebral body to form a space, void or cavity.

In some embodiments, rod 500, or a portion of rod 500, remains in place after restoring vertebral height and, consequently restoring spinal lordosis, to augment the vertebral body. For example, one or more portions of rod 500, e.g. 510 may be selectively detached from the rest of rod 500, and serve as an implant remaining within central portion 50 to augment vertebral body 12. In other embodiments, additional instruments, implants, bone chips, bone cement, and/or other filler materials may be used in conjunction with rod 500 and/or cannula 100 to augment and/or fit vertebral body height.

After using cannula 100 and an instrument such as rod 500 to reposition a vertebral body, some or all of cannula 100 may remain in position. For example, flexible member 120 may be detached from rigid member 110, and rigid member 110 may remain in position within the vertebral body.

As shown in FIGS. 43 and 44, various configurations of instruments and implants may be used. For example a rod or other instrument may have any desired shape, e.g., shapes 610, 620, 630, 640 or 650. Similarly, a rod or other instrument that may be used in conjunction with the partially-flexible cannulae may have any desired curvature, such as is shown for rods 710, 720, 730, and 740. End of rod 740 may include a ball 741.

Augment Vertebral Body (Step 1500)

After repositioning the vertebrae 12 to restore spinal lordosis, and after restoring the height of vertebral body 12b, vertebral body 12b may be augmented using a filler such as, for example, a bone cement, bone chips, demineralized bone, another filler material, or an implant inserted in to the central portion 50 of vertebral body.

Figure 45:
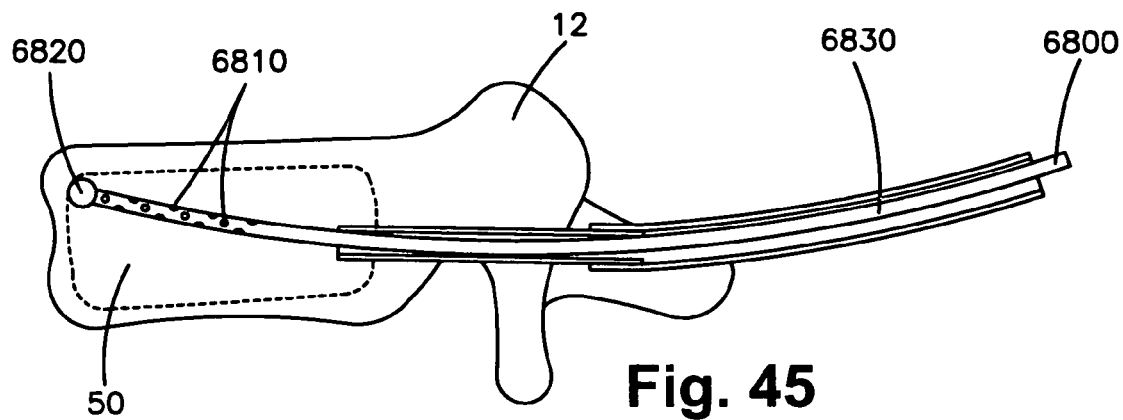
FIG. 45 is a cross-sectional side view illustration of a cannula and an augmentation rod according to another embodiment of the present invention.

FIG. 45 shows a bent rod 6800, which may be used to reposition the vertebra 12b as described above, wherein the rod 6800 may include one or more holes 6810 at near end cap or ball 6820, e.g. the distal end. The holes 6810 may be used to remove bone material from the vertebrae or to introduce a bone cement or other bone filler into space 50, for example in order to fix or augment the restored body. For example, holes 6820 may communicate with a hollow lumen 6830 of rod 6800, through which a bone filler, cement, bone chips, etc. may be injected. It is contemplated that bone filler, bone cement, bone chips, etc. may be inserted simultaneously with rod 6800 to reposition the end plates of the vertebrae, and also that bone filler, bone cement, implants and bone chips, etc. may be inserted within the damaged vertebrae without applying any force to the rod to reposition the endplates.

Figure 46:
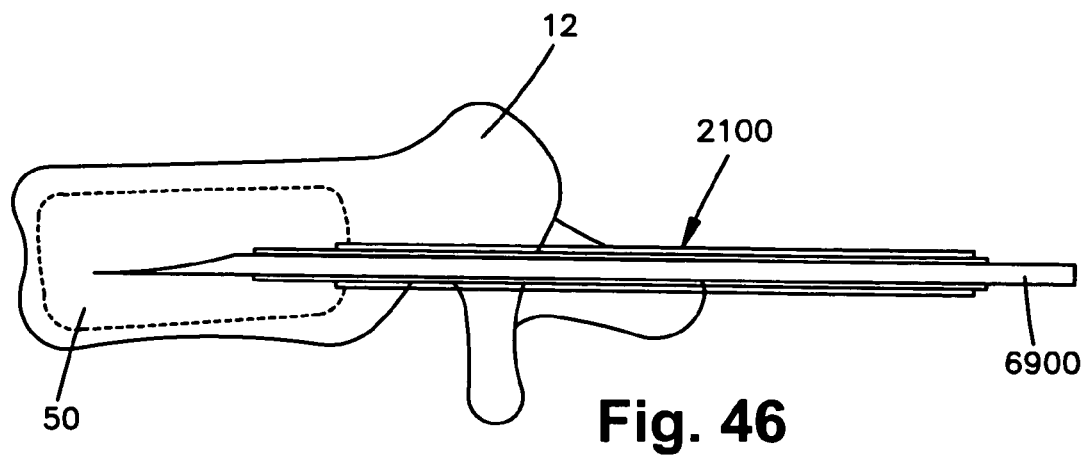
FIG. 46 is a cross-sectional side view illustration of a needle and catheter positioned through a cannula according to the present invention.

In other embodiments, as shown in FIG. 46, curved instrument, e.g. curved rod may be removed from the vertebra 12b. A needle 6900 and/or a catheter or cannula may then be inserted through cannula 2100, e.g., in order to inject a bone filler, bone chips, a bone cement, or the like into the vertebrae. Bone filler, bone chips, bone cement, implants or other augmentation devices may be inserted into the vertebrae with or without first repositioning the end plates of the damaged vertebrae, and, may be inserted under sufficient force to reposition the vertebral end plates without a further instrument or device assistance.

In some embodiments, a desired filler material may be too thick or comprise particles that are too large to be delivered through a rod 6800 as shown in FIG. 45 or a syringe needle 6900 as shown in FIG. 46. In such cases, particulate or other non-fluid filler material can be inserted into vertebral body 12b by other means, for example using a spiral conveyor or other device to deliver the filler material.

Figure 47A:
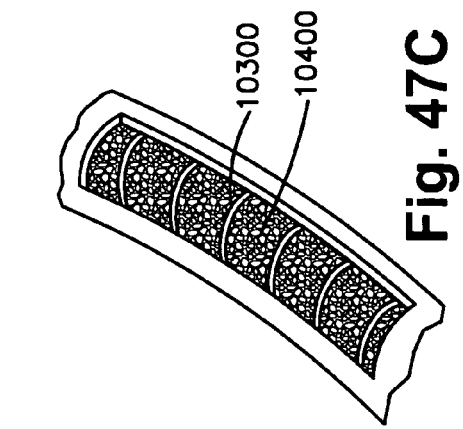
FIGS. 47A-C are perspective view illustrations of apparatus that may be adapted for delivering a vertebral body filler material according to an embodiment of the present invention.
Figure 47B:
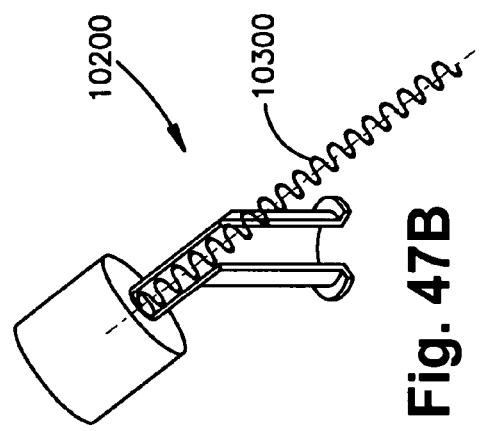
Figure 47C:
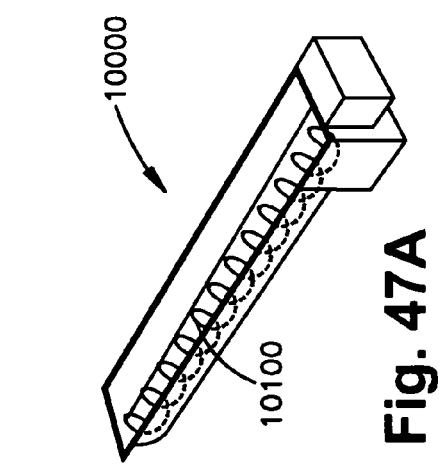

FIG. 47 shows examples of devices 10000 and 10100 comprising spiral conveyors 10200 (MEVA Shaftless Screw Conveyor, VoR Environmental, Botany, NSW, Australia) and 10300 (Spiroflow Flexible Screw Conveyor, Spiroflow Inc., Monroe, N.C.) that are commercially available for delivering particulate material 10400. Screw features of such spiral conveyor devices may be adapted or employed to deliver filler material to augment a vertebral body 12. Such a spiral conveyor mechanism may, for example, provide delivery of filler material under lower pressure than, for example, injecting with a syringe. Lower pressures during augmentation of a fractured vertebra may help avoid leakage of the filler material.

Figure 48:
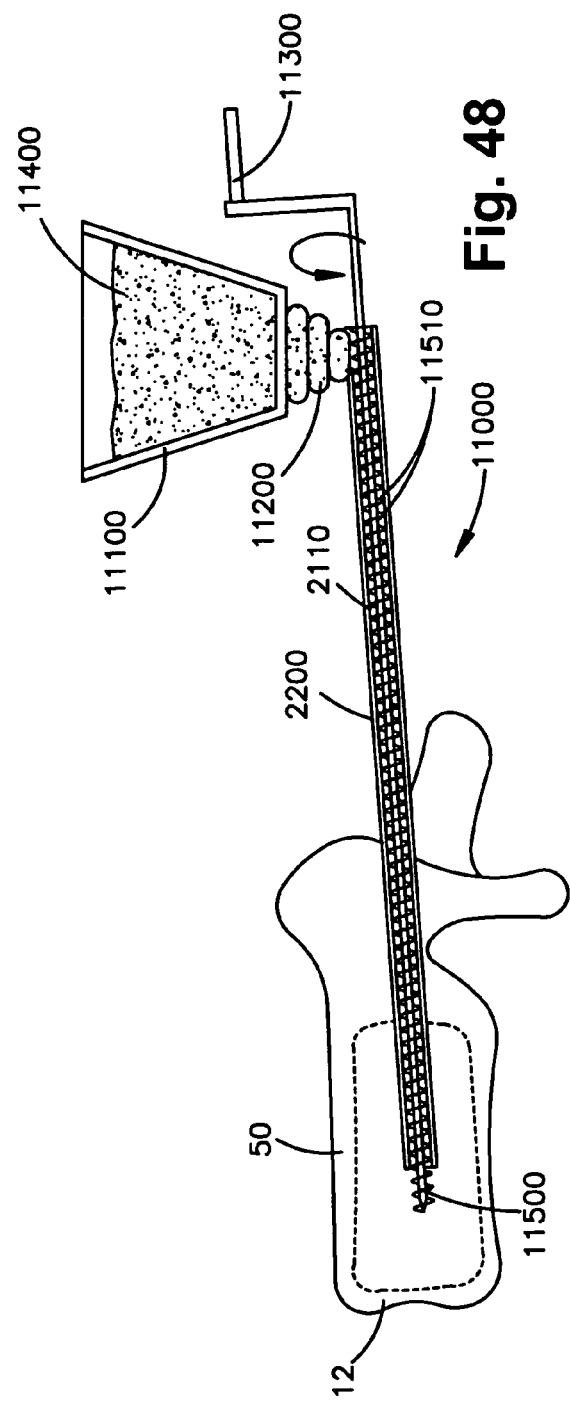
FIG. 48 is a schematic side view illustration of an apparatus for augmenting a vertebral body with a filler material.

FIG. 48 shows an example of a spiral conveyor device 11000 for in use for augmenting a vertebral body 12. A hopper 11100 may be adapted to hold filler material to be inserted into the vertebral body, for example through cannula 2100 which is inserted into vertebral body as described above. Hopper 11100 may communicate with lumen 2110 of cannula 2100, for example through a valve 11200. A screw 11500 may passes through cannula 2200 from valve 11200 and in to the central portion 50 of vertebral body 12. A crank 11300 or other mechanism may be rotated, e.g., manually or using a motor (not shown), to turn screw 11500. During rotation, filler material 11400 from hopper 11100 may enter spaces between threads 11510 of screw 11500 and be delivered along the length of screw 11500 and into space 50.

One skilled in the art will appreciate that each of the steps, methods and apparatus described herein may be used in various combinations and/or in conjunction with various other methods and apparatus. For example, a kit for performing one or more steps or portions of the methods described herein may comprise, in one or more packages, various combinations of assemblies and components described herein. A kit may include, for example, one or more cannulae, disruption devices, external fixators, and implants or filler materials for augmenting bone. Such embodiments may also comprise one or more syringes, conveyors or other apparatus for injecting a fluid, semi-viscous fluid or non-fluid filler material into a vertebral body.

Figure 49:
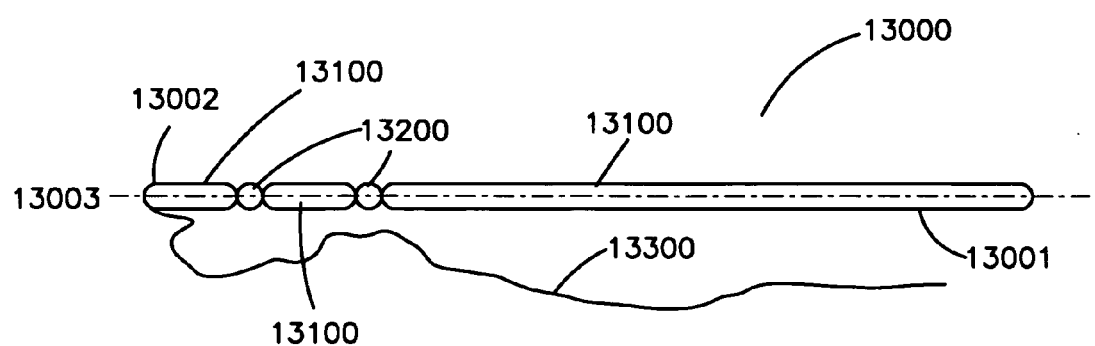
FIG. 49 is a perspective view of an embodiment of an instrument of the present invention.

In another embodiment for augmenting a vertebral body, an instrument 13000 as shown in FIG. 49 can be used for the minimally invasive lordotic correction of the spine. The instrument 13000 may include at least two body segments 13100 which are connected together with joints 13200. The joints between the body segments are preferably ball joints, universal joints, or some other type of joint. Preferably, the joints permit the body segments to polyaxially rotate with respect to each other, or at least provide rotation or pivoting about an axis. The body segments 13100 may be cylindrical in shape. Alternatively, the body segments may be flat or have other cross-sectional shapes. The body segments are preferably rigid so that a pushing force applied to the proximal end 13001 of the instrument 13000 will be transmitted to the distal end 13002. The elongated element 13300 may be made from a metal, a polymer ceramic, composite materials, or combinations thereof.

Furthermore, it will be appreciated by those skilled in the art that the length of the body segments may vary. A wire, thread, or other elongated element, preferably a flexible elongated element 13300 may be connected to the foremost or distal body segment 13100a. The term foremost or distal part of the instrument 13000 refers to the end 13002 of the instrument that is located away from the portion handled by the surgeon. Whereas, the rear end, back end, or distal end 13001 of the instrument 13000 refers to the end of the instrument not located in the body of the vertebrae which is handled by the surgeon.

In its normal or at rest position, when no forces are applied to the elongated element 13300, the body segments 13100 and joints 13200 preferably are configured such that the body segments 13100 are aligned along a straight line or longitudinal axis 13003 of the instrument 13000. When the elongated element 13300 is pulled, the body segments 13100 at the distal end 13002, where the elongated element 13300 is attached, no longer coincides with the longitudinal axis 13003, such that a bend 13004 in the instrument appears.

Figure 50:
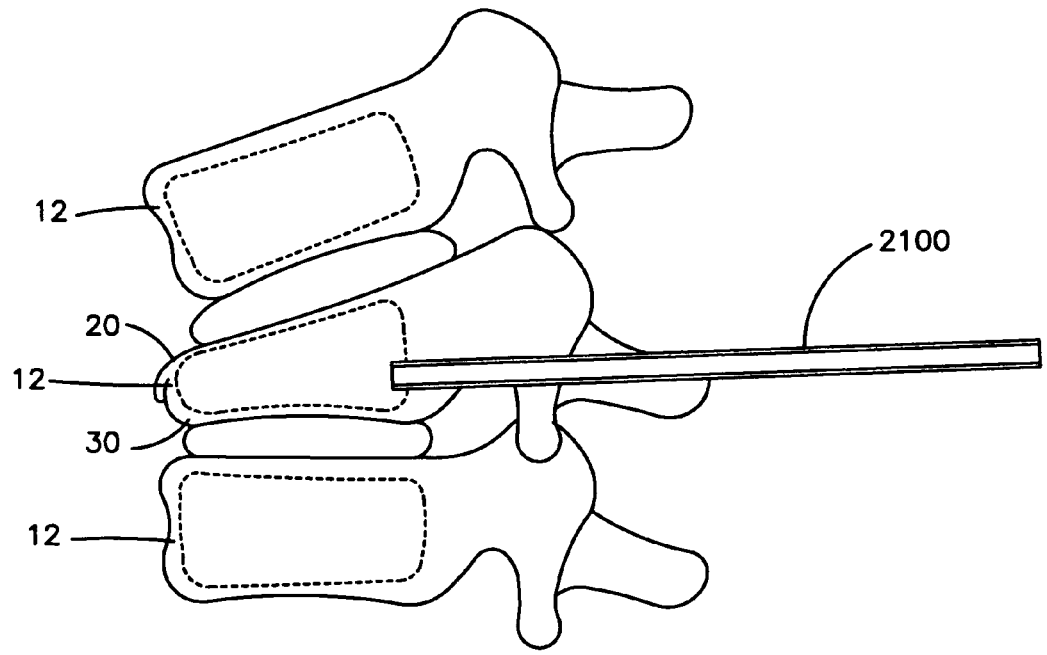
FIG. 50 is a perspective view a cannula inserted through the pedicles of a fractured vertebral body.
Figure 51:
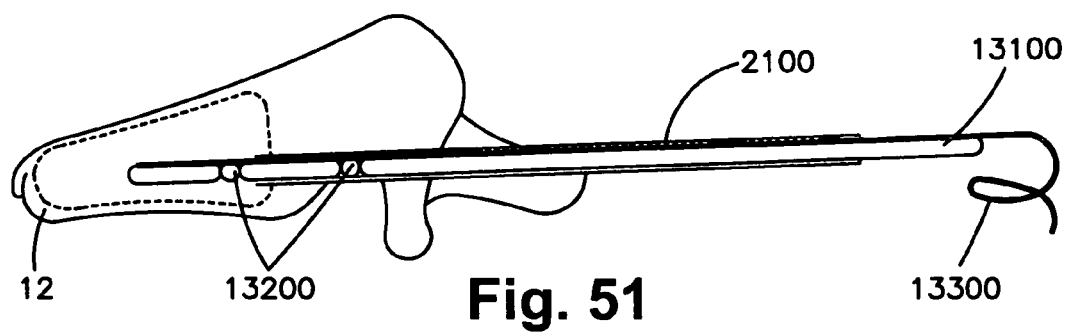
FIG. 51 is a perspective view of the instrument depicted in FIG. 49 inserted into the cannula of FIG. 50.
Figure 52:
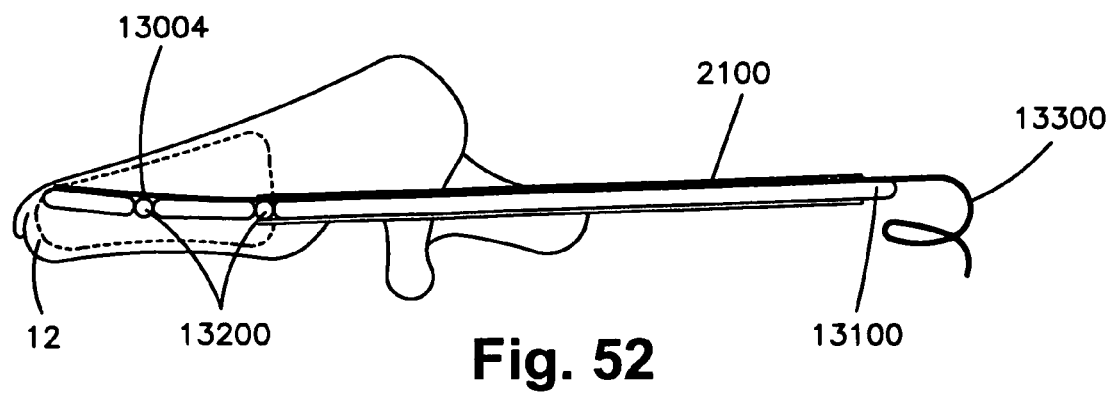
FIG. 52 is a perspective view of the instrument depicted in FIG. 49 with its front end lifted.
Figure 53:
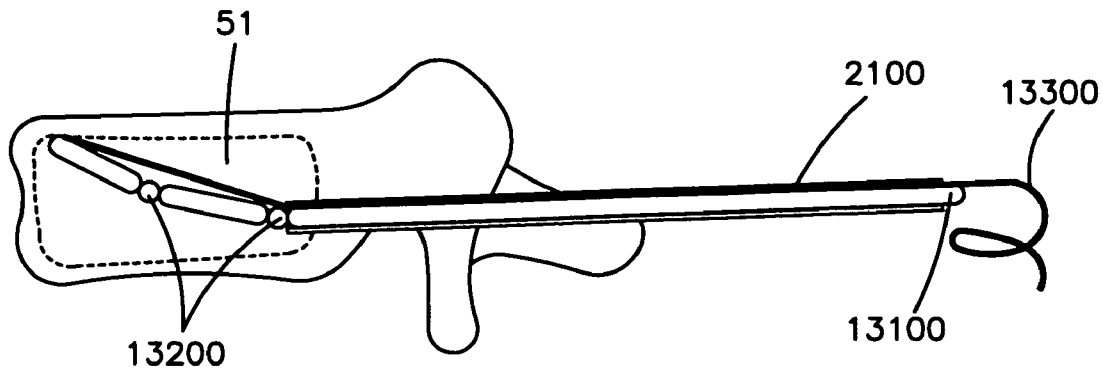
FIG. 53 is a perspective view of the vertebral body restored to its original height.

To use the instrument 13000, a cannula 2100 is inserted through the pedicles of the broken vertebral body 12 (FIG. 50). The instrument 13000 is inserted through the cannula 2100 such that the distal end 13002 of the instrument 13000 is positioned within the body of the collapsed vertebrae 12 (FIG. 51). The instrument 13000 is inserted down the cannula 2100 by exerting a pushing force on the proximal end 13001. The instrument 13000 is sufficiently stiff so that the force is transmitted along the instrument 13000 to move it within the cannula 2100 and into the vertebral body. The distal end 13002 of the instrument 13000 can then be bent/lifted by pulling at the elongated element 13300 (FIG. 52) in a direction toward the proximal end 13001 of the instrument 13000. If enough force is applied, the endplates 20, 30 of the collapsed vertebral body 12 may be pushed apart as a result of the body segments 13100 applying a force to the endplates 20, 30, and the vertebral body may be restored to its original height (FIG. 48). Additionally, the bone in the vertebral body 12 around the distal end 13002 of the instrument 13000, or most distal body segment 13100a gets compacted, which may reduce the risk of cement leakage. The moving of the endplates 20, 30 and/or compacting of the bone may create a cavity 51 in the vertebrae.

Figure 54:
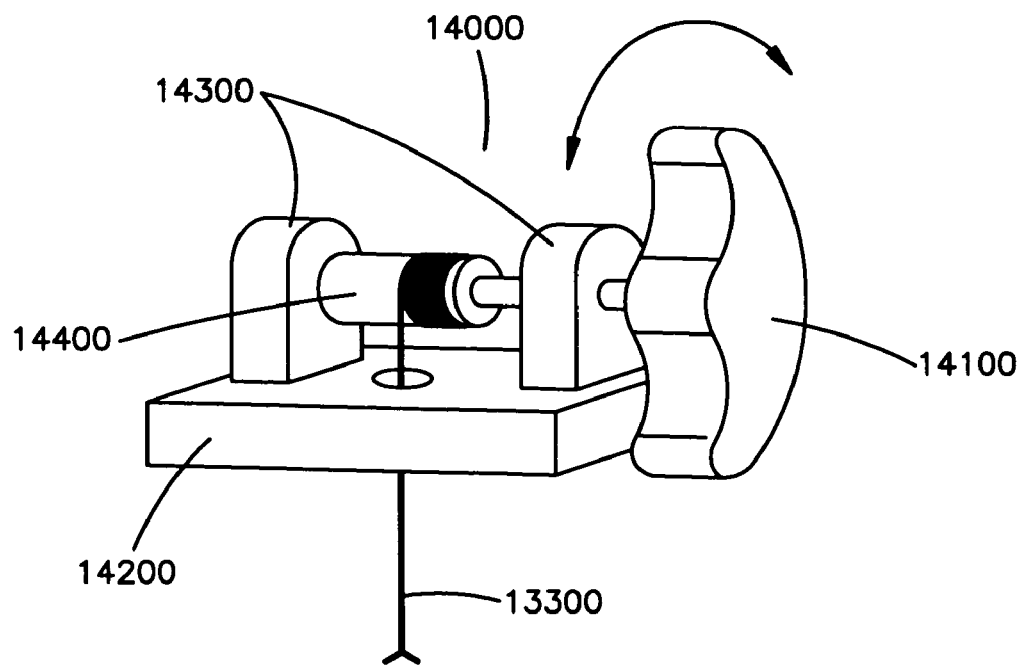
FIG. 54 is a perspective view of a mechanism to pull the wire of the instrument depicted in FIG. 49.
Figure 55:
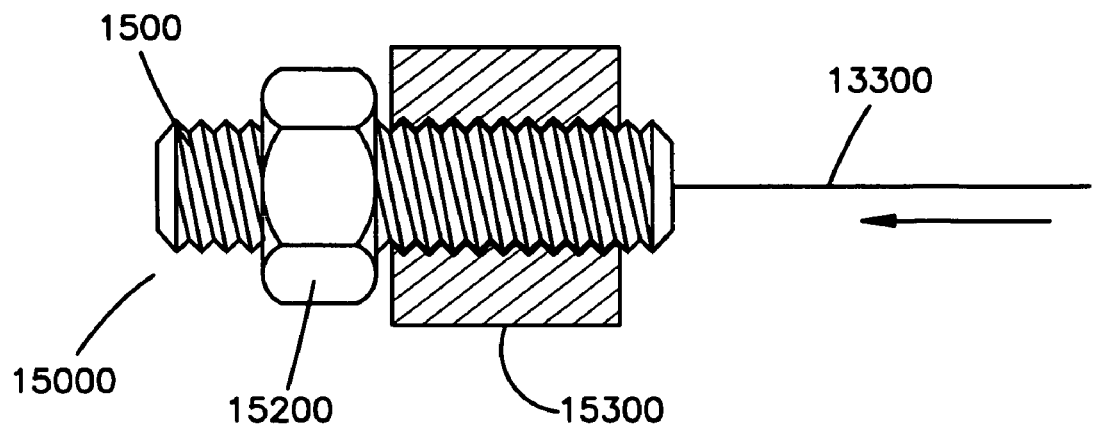
FIG. 55 is a perspective view of another exemplary embodiment of a mechanism to pull the wire of the instrument depicted in FIG. 49.
Figure 56:
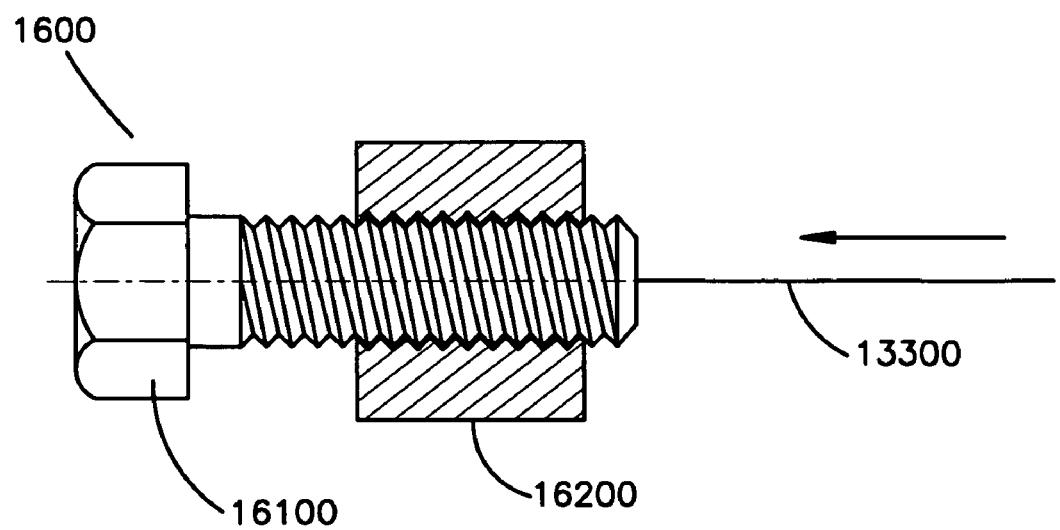
FIG. 56 is a perspective view of another exemplary embodiment of a mechanism to pull the wire of the instrument depicted in FIG. 49.

FIGS. 54-56 depict different mechanisms to pull the elongated element 13300 of the instrument 13000. These different mechanisms may form a part of the instrument 13000 or be a separate assembly used in conjunction with the instrument 13000.

FIG. 54 shows a kind of bobbin 14000 that may be used to pull the elongated element 13300. The bobbin 14000 may include two supports 14300 attached to a platform 14200 with an axle 14400 attached to the two supports 14300. A knob 14100 is attached to the axle and may be used to rotate the axle, pulling the elongated element 13300 thereby lifting the distal end 13002 of the instrument 13000.

FIG. 55 depicts a screw nut assembly 15000. The screw nut assembly 15000 may form a rear part of the instrument 13000 or be attached to the proximal end 13001 of the instrument 13000. The screw nut assembly 15000 may include a threaded shaft 15100, a nut 15200, and a casing 15300. The elongated element 13300 may be connected to the threaded shaft 15100. By turning the screw nut assembly, the elongated element 13300 is pulled back as result of the threaded shaft 15100 moving with respect to the nut 15200 and casing 15300, thereby lifting the distal end 13002 of the instrument 13000. As the distal segment 13100a is bent and lifted, the body segments 13100 articulate with respect to each other as a result of movement permitted by the joints 13200. A biasing force may be applied by the joints 13200, by, for example, a spring member, to keep the body segments biased to the normal, at rest position, where the body segments 13100 are aligned in a straight line or along the longitudinal axis 13003. While the longitudinal axis 13003 has been shown as a straight line, it can be appreciated that the longitudinal axis 13003 may also be curved.

Similarly, FIG. 56 depicts a screw assembly 16000. The screw assembly 16000 may include a screw 16100 and a casing 16200. One end of the elongated element 13300 is connected to the screw 16100. As the screw 16100 is turned, the elongated element 13300 is correspondingly pulled back, thereby lifting the distal end 13002 of the instrument 13000.

Figure 57A:
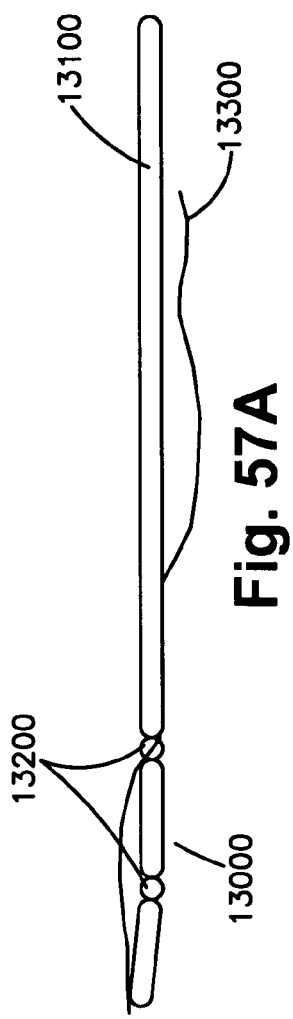
FIGS. 57A-C are perspective views of other exemplary embodiments of the instrument of the present invention.
Figure 57B:
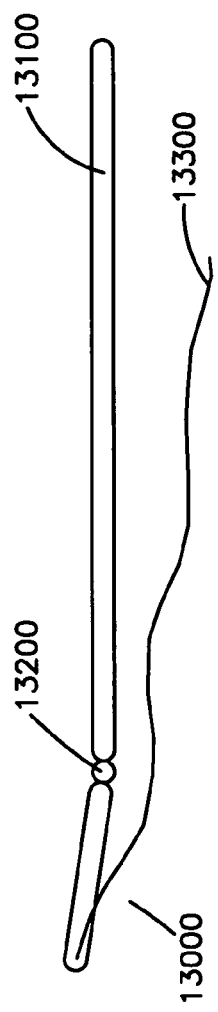
Figure 57C:
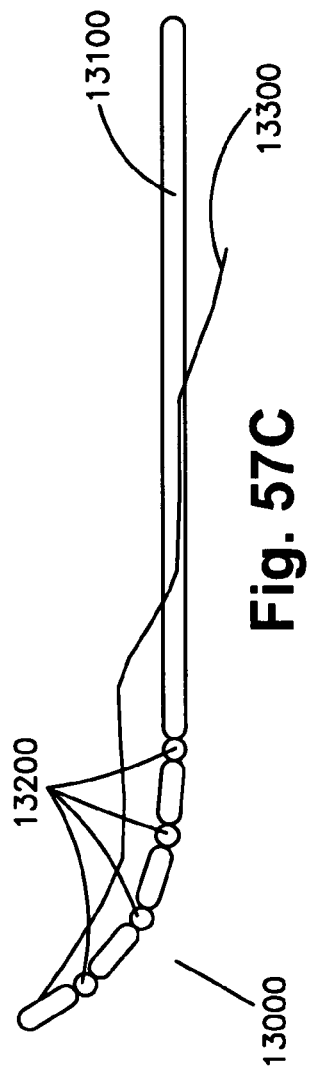

FIGS. 57A-C depict other configurations of the instrument 13000. Depending on the application, the number of body segments 13100 and joints 13200 may vary. FIG. 57A shows an instrument 13000 with three body segments 13100 and two joints 13200. FIG. 57B shows an instrument 13000 with two body segments 13100 and one joint 13200, and FIG. 57C shows an instrument 13000 with five body segments 13100 and four joints 13200.

Figure 58B:
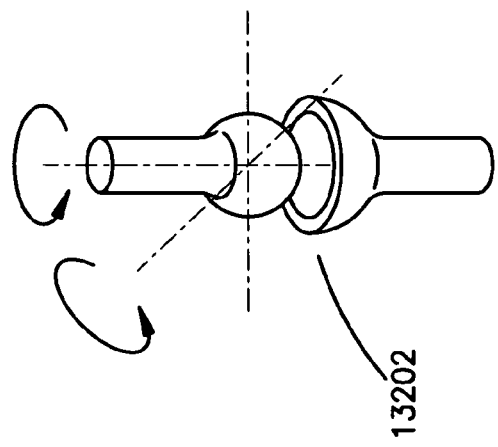
FIGS. 58A and 58B are perspective views of exemplary embodiments of ball joints of the instrument depicted in FIG. 49.
Figure 58A:
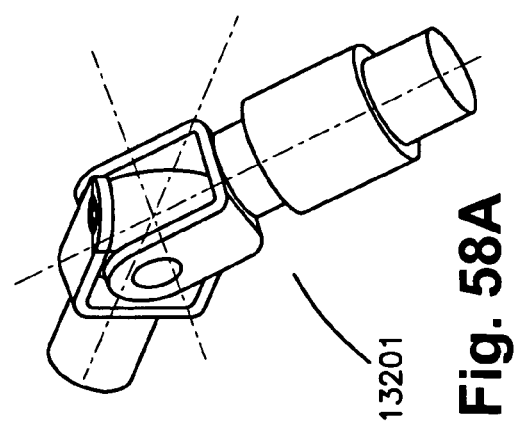

FIGS. 58A and 58B depict two different types of joints 13200 that may be used. FIG. 58A illustrates an universal joint 13201, and FIG. 58B illustrates a ball joint 13202. However, it is contemplated that other types and configurations of joints may be used. It will be appreciated by those skilled in the art that the joint 13200 may be sized and configured to rotate about the x, y, and/or z axis.

Figure 59:
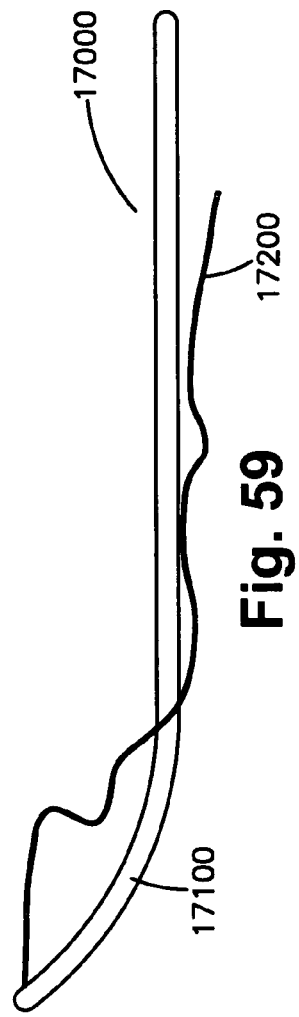
FIG. 59 is a perspective view of another exemplary embodiment of the instrument of the present invention.

In an alternative embodiment of the present invention, the instrument 1700 may be constructed from a polymer, without a joint(s) or from a memory alloy (e.g. Nitinol) (FIG. 59). As the elongated element 17200 is pulled, the distal end of the segment 17100 of the instrument 17000 is bent upwards so that the distal end is laterally offset from the original position along the longitudinal axis of the instrument to thereby push the endplates of the collapsed vertebral body apart and restore the vertebral body to its original height.

Figure 60:
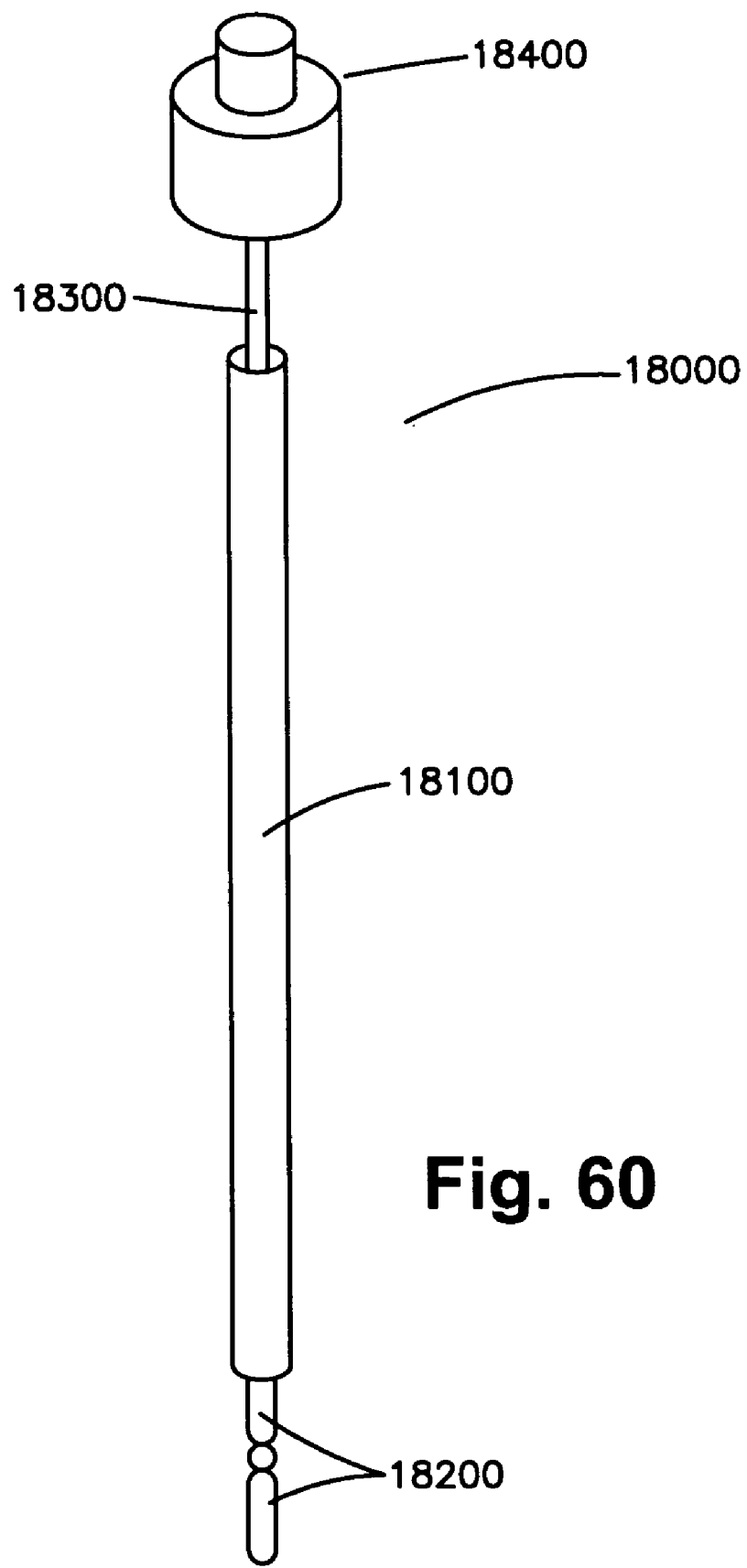
FIG. 60 is another perspective view of an exemplary embodiment of the instrument of the present invention.

In yet another embodiment of the invention, the instrument 18000, depicted in FIG. 60 may comprise a main body segment 18100, at least one adjustable segment 18200 (FIG. 60 depicts two adjustable segments), and an elongated element 18300. The instrument 18000 also may include a mechanism 18400 for pulling the elongated element 18300, thereby lifting the adjustable segment 18200.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Although the apparatus and methods described herein thus far have been described in the context of repositioning, disrupting and augmenting vertebrae in the context of vertebral compression fractures and deformations in spinal curvature, various other uses and methods are envisioned, such as for example repositioning and augmenting long bones, ribs, and other bony skeletal structures. Further, in some embodiments, a partially flexible catheter may be used to insert an implant, e.g., one or more flexible chains of linked bodies. A bone cement, bone chips or other filler may also be used to aid augmentation. In other embodiments, another implant 3430 may be inserted.

In some embodiments, the implants and methods described herein may be used in conjunction with other apparatus and methods to restore lordosis and augment vertebral body. For example, one or more partially flexible cannula 100 may be used in conjunction with other known procedures, e.g., vertebroplasty or a balloon kyphoplasty, that may be used to begin repositioning of a vertebral body and/or create a space within the body for the implants.

In other embodiments, various minimally invasive implants and methods for alleviating discomfort associated with the spinal column may employ anchors and other implants described herein. For example, an implant comprising one or more linked bodies, for example within an expandable container (not shown), may be implanted between spinous processes of adjacent vertebrae to distract the processes and alleviate pain and other problems caused for example by spinal stenosis, facet arthropathy, and the like. For example, augmentation systems described herein may be used instead of or in addition to expandable interspinous process apparatus and methods described in U.S. Patent Publication No. 2004/018128 and U.S. patent application Ser. No. 6,419,676 to Zucherman et al.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. The presently disclosed embodiments are therefore to be considered in all respects as illustrative and not restrictive, the scope of the invention being indicated by the appended claims, and not limited to the foregoing description.

What is claimed is:

1. A method for treating a damaged vertebral body and restoring lordosis, the method comprising:
   (a) inserting a first end of a first elongated member into a first vertebral body;
   (b) inserting a first end of a second elongated member into a second vertebral body, wherein the first and second vertebral bodies are adjacent the damaged vertebral body;
   (c) coupling a second end of the first elongated member to a fixation rod and securing the second end of the first elongated member to the fixation rod with a first clamp;
   (d) coupling a second end of the second elongated member to the fixation rod and securing the second end of the second elongated member to the fixation rod with a second clamp;
   (e) moving at least one of the first and second elongated members relative to one another to change the position of at least one of the first and second vertebral bodies with respect to away from the damaged vertebral body and maintaining the at least one of the first and second vertebral bodies away from the damaged vertebral body;
   (f) inserting a cannula, via a posterior approach, into the damaged vertebral body, the cannula having a lumen dimensioned to provide a passage into the damaged vertebral body;
   (g) inserting a disruption device through the lumen of the cannula and into the damaged vertebral body;
   (h) fracturing a sidewall of the damaged vertebral body using the disruption device;
   (i) restoring a height of the damaged vertebral body to restore lordosis; and
   (j) augmenting the vertebral body.

2. The method of claim 1, wherein step (e) comprises:
   disengaging the first clamp from the fixation rod;
   pivoting the first elongated member; and
   reengaging the first clamp to the fixation rod to fix the position of the first vertebral body.

3. The method of claim 1, wherein step (e) comprises moving the position of the first and second clamps connected to the first and second elongated members, respectively, along the longitudinal axis of the fixation rod.

4. The method of claim 1, wherein step (i) comprises:
   inserting a tool through the cannula and into the damaged vertebral body; and
   moving an endplate of the damaged vertebral body with the tool to restore the height of the damaged vertebral body.

5. The method of claim 4, wherein:
   the tool comprises a curved rod having a longitudinal axis and a distal end configured to contact bone; and
   step (i) comprises advancing the distal end of the curved rod through the cannula and into contact with the endplate, and moving the endplate away from an opposite endplate of the vertebra to reposition the vertebra endplate by applying a force along the longitudinal axis of the curved rod.

6. The method of claim 4, wherein the distal end of the tool contacts the end plate of the damaged vertebral body from the inside of the damaged vertebral body to move the end plate.

7. The method of claim 1, wherein steps (f) through (h) are performed before steps (a) and (b).

8. The method of claim 1, wherein step (j) comprises:
   injecting a filler material from at least one of the group consisting of bone cement, bone chips, demineralized bone, or an implant.

9. The method of claim 1, wherein the fixation rod is arcuate shaped.

10. The method of claim 1, wherein the steps (f) through (h) are performed before steps (a) through (e).

11. The method of claim 1, wherein step (f) includes inserting the cannula through the pedicle of the damaged vertebrae and into the body of the vertebrae.

12. The method of claim 1, wherein the side wall of the anterior portion of the damaged vertebral body is fractured while a distal end of the disruption device is located within the damaged vertebral body.

13. The method of claim 1, wherein the first end of the first elongated member is inserted into the first vertebral body via a posterior approach.

14. The method of claim 1, wherein the first elongated member comprises a cannula.

15. A method for treating a damaged vertebral body, comprising:
   (a) inserting a first end of a first elongated member into a first vertebral body;
   (b) inserting a first end of a second elongated member into a second vertebral body, wherein the first and second vertebral bodies are adjacent the damaged vertebral body;
   (c) coupling a second end of the first elongated member to a fixation rod and securing the second end of the first elongated member to the fixation rod with a first clamp;
   (d) coupling a second end of the second elongated member to the fixation rod and securing the second end of the second elongated member to the fixation rod with a second clamp;
   (e) moving at least one of the first and second elongated members relative to one another to change the position of at least one of the first and second vertebral bodies away from the damaged vertebral body and maintaining the at least one of the first and second vertebral bodies away from the damaged vertebral body;
   (f) inserting a cannula into the damaged vertebral body, the cannula having a lumen dimensioned to provide a passage into the damaged vertebral body;
   (g) inserting a disruption device through the lumen of the cannula and into the damaged vertebral body;
   (h) fracturing a sidewall of the damaged vertebral body using the disruption device;
   (i) restoring a height of the damaged vertebral body; and
   (j) augmenting the vertebral body.

16. The method of claim 15, wherein step (e) comprises:
   disengaging the first clamp from the fixation rod;
   pivoting the first elongated member; and
   reengaging the first clamp to the fixation rod to fix the position of the first vertebral body.

17. The method of claim 15, wherein step (e) comprises moving the position of the first and second clamps connected to the first and second elongated members, respectively, along the longitudinal axis of the fixation rod.

18. The method of claim 15, wherein step (i) comprises:
   inserting a tool through the cannula and into the damaged vertebral body; and
   moving an endplate of the damaged vertebral body with the tool to restore the height of the damaged vertebral body.

19. The method of claim 18, wherein:
   the tool comprises a curved rod having a longitudinal axis and a distal end configured to contact bone; and
   step (i) comprises advancing the distal end of the curved rod through the cannula and into contact with the endplate, and moving the endplate away from an opposite endplate of the vertebra to reposition the vertebra endplate by applying a force along the longitudinal axis of the curved rod.

20. The method of claim 18, wherein the distal end of the tool contacts the end plate of the damaged vertebral body from the inside of the damaged vertebral body to move the end plate.

21. The method of claim 15, wherein steps (f) through (h) are performed before steps (a) and (b).

22. The method of claim 15, wherein step (j) comprises:
injecting a filler material from at least one of the group consisting of bone cement, bone chips, demineralized bone, or an implant.

23. The method of claim 15, wherein the fixation rod is arcuate shaped.

24. The method of claim 15, wherein the steps (f) through (h) are performed before steps (a) through (e).

25. The method of claim 15, wherein step (f) includes inserting the cannula through the pedicle of the damaged vertebrae and into the body of the vertebrae.

26. The method of claim 15, wherein the side wall of the anterior portion of the damaged vertebral body is fractured while a distal end of the disruption device is located within the damaged vertebral body.

27. The method of claim 15, wherein the first end of the first elongated member is inserted into the first vertebral body via a posterior approach.

28. The method of claim 15, wherein the first elongated member comprises a cannula.

29. The method of claim 15, wherein the cannula and the first end of the second elongated member is inserted into the second vertebral body via a posterior approach.

* * * * *